(12) United States Patent
Wolleschensky et al.

(10) Patent No.: US 7,485,875 B2
(45) Date of Patent: Feb. 3, 2009

(54) RESOLUTION-ENHANCED LUMINESCENCE MICROSCOPY

(75) Inventors: Ralf Wolleschensky, Jena (DE); Michael Kempe, Kunitz (DE)

(73) Assignee: Carl Zeiss MicroImaging GmbH, Jena (DE)

( * ) Notice: Subject to any disclaimer, the term of this patent is extended or adjusted under 35 U.S.C. 154(b) by 373 days.

(21) Appl. No.: 11/491,781

(22) Filed: Jul. 24, 2006

(65) Prior Publication Data
US 2007/0023686 A1 Feb. 1, 2007

Related U.S. Application Data

(60) Provisional application No. 60/702,342, filed on Jul. 25, 2005.

(30) Foreign Application Priority Data
Jul. 22, 2005 (DE) .................. 10 2005 034 443

(51) Int. Cl.
*G21H 3/02* (2006.01)
*G01N 21/64* (2006.01)
(52) U.S. Cl. ................................. 250/458.1; 356/317
(58) Field of Classification Search ............. 250/458.1; 359/385
See application file for complete search history.

(56) References Cited

U.S. PATENT DOCUMENTS 5,731,588 A 3/1998 Hell et al.

(Continued)

FOREIGN PATENT DOCUMENTS

| DE | 197 02 753 A1 | 7/1998 |
|---|---|---|
| DE | 103 25 460 A1 | 11/2004 |

OTHER PUBLICATIONS

Pawley, James B., *Handbook of Biological Confocal Microscopy*, Chapter 14, "Visualization Systems for Multidimensional CLSM Images," Plenum Press, pp. 211-254 (1995).

(Continued)

*Primary Examiner*—David P Porta
*Assistant Examiner*—Jessica L Eley
(74) *Attorney, Agent, or Firm*—Patterson, Thuente, Skaar & Christensen, P.A.

(57) ABSTRACT

A resolution-enhanced luminescence microscopy method, wherein a sample is excited so as to luminesce, and thus to emit a given luminescence radiation, by irradiation of exciting radiation and an image of the luminescent sample is obtained, wherein the luminescent sample is transferable from a first state of luminescence, in which first state the sample's excitability for emission of the given luminescence radiation increases up to a maximum value as the exciting radiation power increases, into a second state of luminescence, in which second state the sample has reduced excitability for emission of the given luminescence radiation relative to the first state, wherein the maximum value is assigned to a threshold value of exciting radiation power and the sample is transferable into the second state by irradiation of exciting radiation power above the threshold value, the sample being brought into the first state in partial areas and being brought into the second state in adjacent partial areas by irradiating exciting radiation with an exciting radiation distribution having at least one spatial power maximum above the threshold value, the image of the luminescent sample comprising sample areas being in the first state and sample areas being in the second state, sample areas being in the first state contributing predominantly to the image and the image thus having an enhanced spatial resolution with respect to the exciting radiation distribution.

30 Claims, 15 Drawing Sheets

U.S. PATENT DOCUMENTS

| | | | |
|---|---|---|---|
| 5,866,911 | A | 2/1999 | Baer |
| 6,633,432 | B2 | 10/2003 | Iketaki |
| 6,909,105 | B1 | 6/2005 | Heintzmann et al. |
| 2001/0045523 | A1* | 11/2001 | Baer .................. 250/459.1 |
| 2004/0197267 | A1* | 10/2004 | Black et al. .............. 424/9.6 |
| 2006/0033987 | A1 | 2/2006 | Stelzer et al. |
| 2006/0038993 | A1* | 2/2006 | Hell ........................ 356/318 |
| 2008/0118912 | A1* | 5/2008 | Dickson et al. .............. 435/6 |

OTHER PUBLICATIONS

Pawley, James B., *Handbook of Biological Confocal Microscopy*, Chapter 16, "Fluorophores for Confocal Microscopy," Plenum Press, pp. 267-279 (1995).

Hell, Stefan W., "Concepts for nanoscale resolution in fluorescence microscopy," *Current Opinion in Neurobiology*, vol. 14, pp. 599-609 (2004).

Heintzmann, Rainer, "Saturated patterned excitation microscopy-a concept for optical resolution improvement," *J. Opt. Soc. Am. A*, vol. 19, No. 8, pp. 1599-1609 (Aug. 2002).

Ryoko Ando, et al., "Regulated Fast Nucleocytoplasmic Shuttling Observed by Reversible Protein Highlighting,"*Science*, vol. 306 (pp. 1370-1373) Nov. 19, 2004.

CoralHue Dronpa Green (pDG1-S2), MBL Group Company, Code No. AM-V0071, www.mblint.com.

* cited by examiner

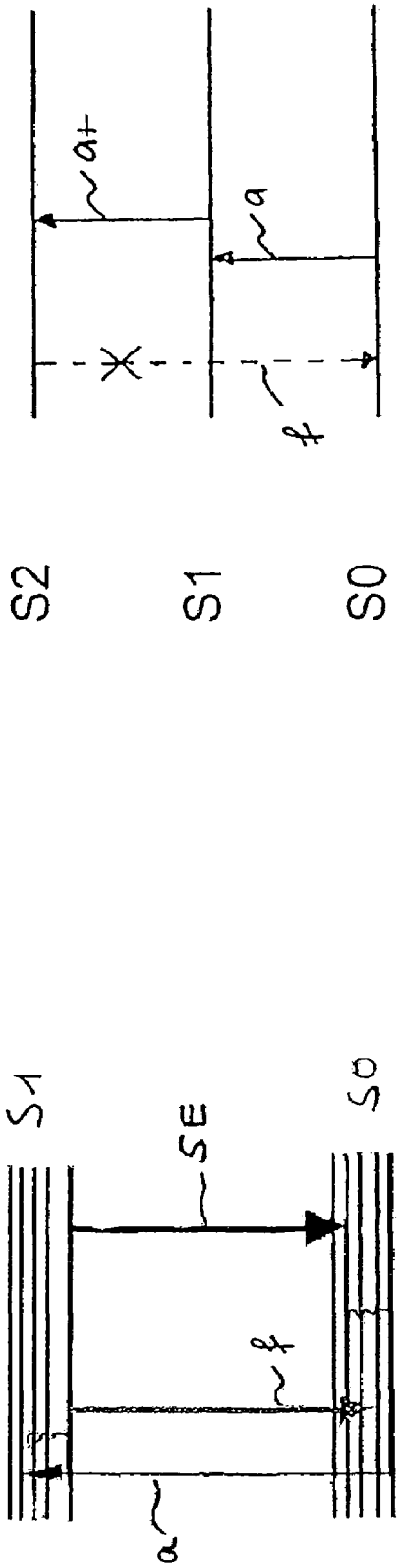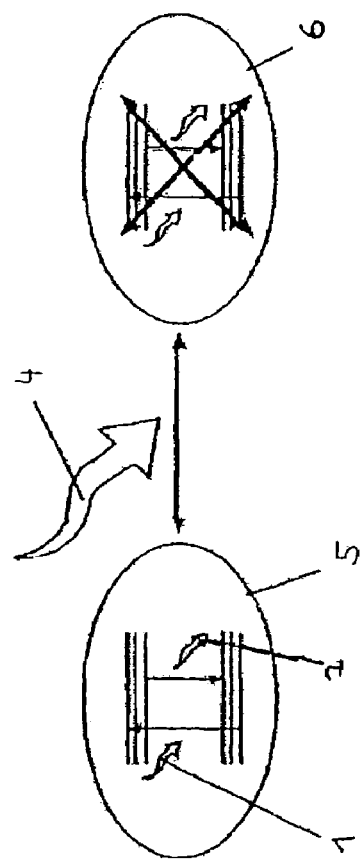

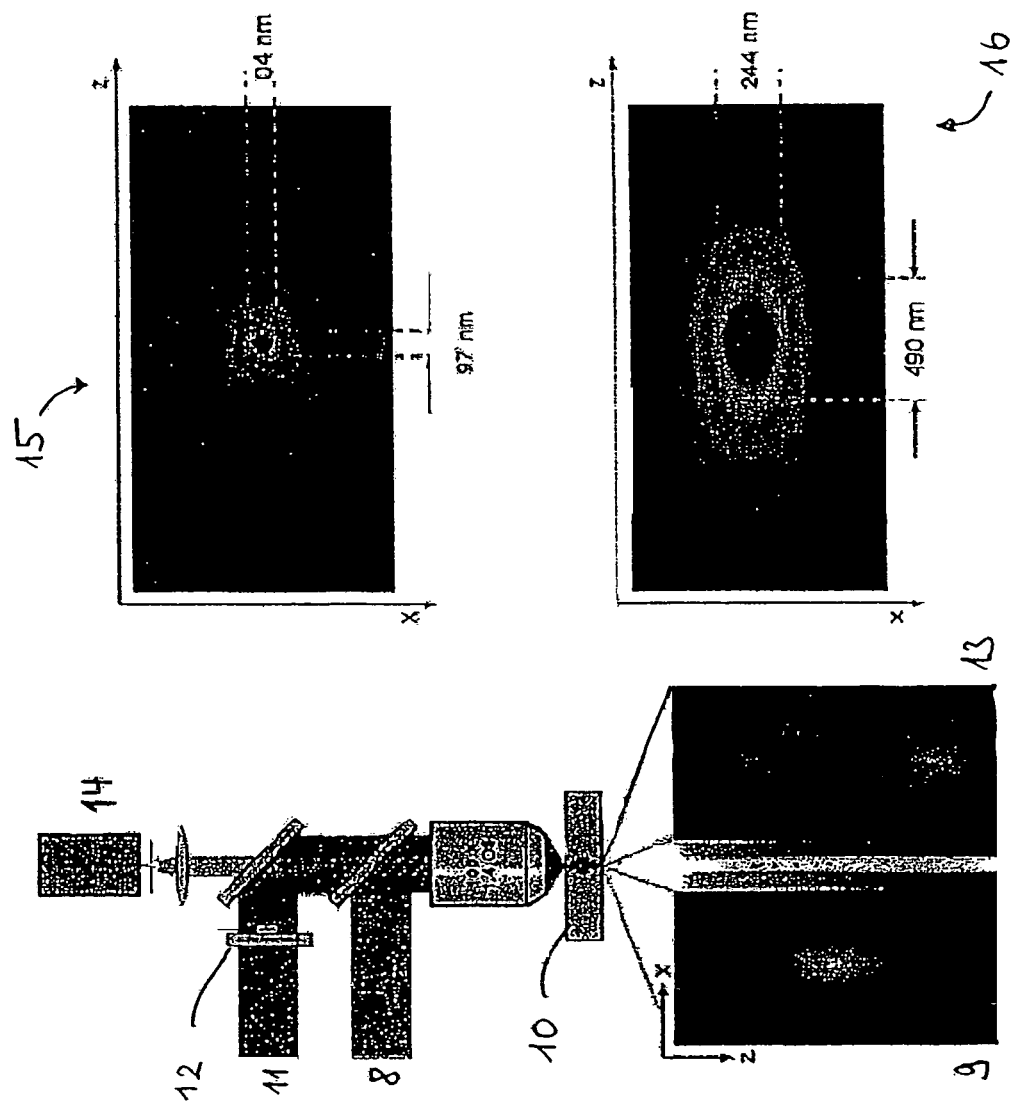

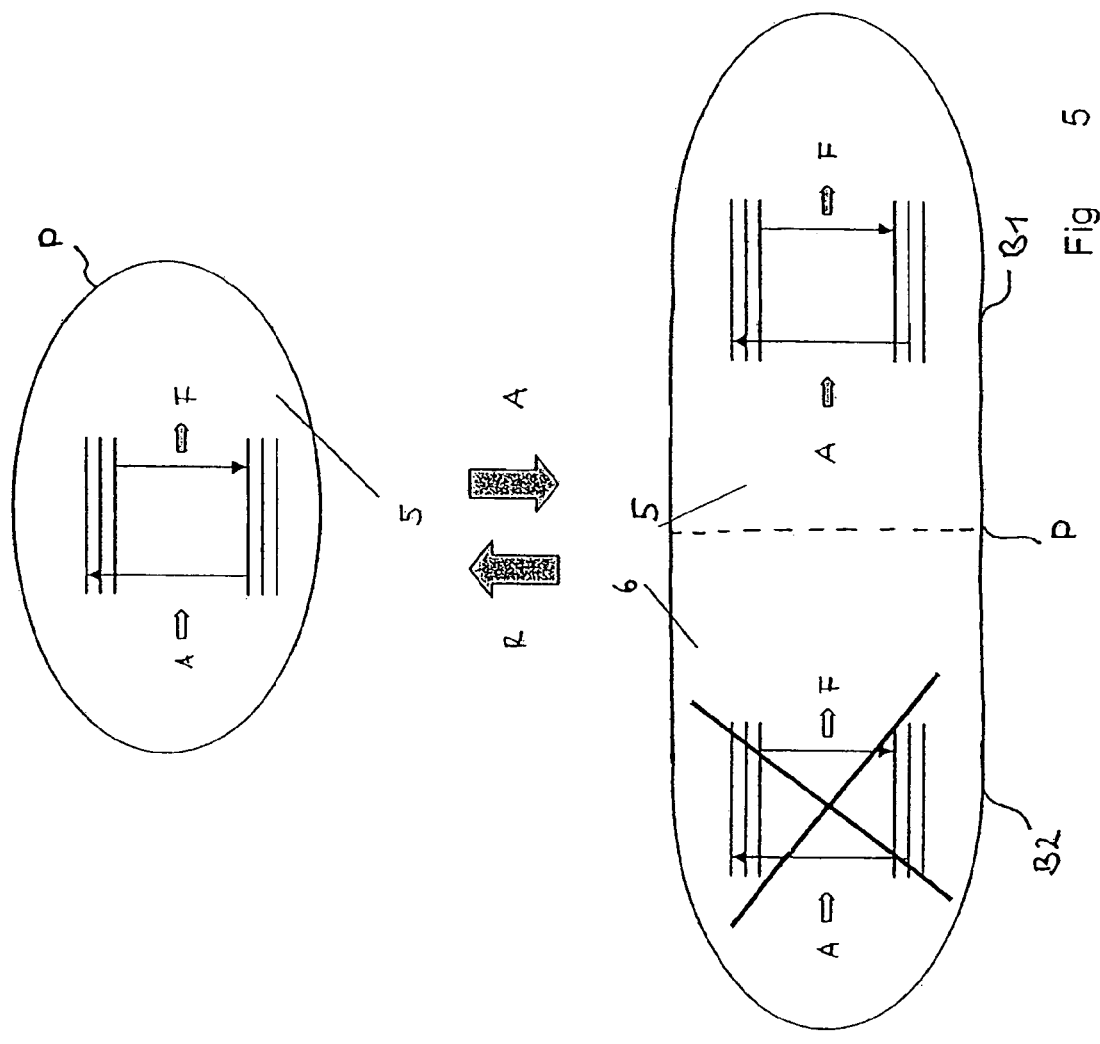
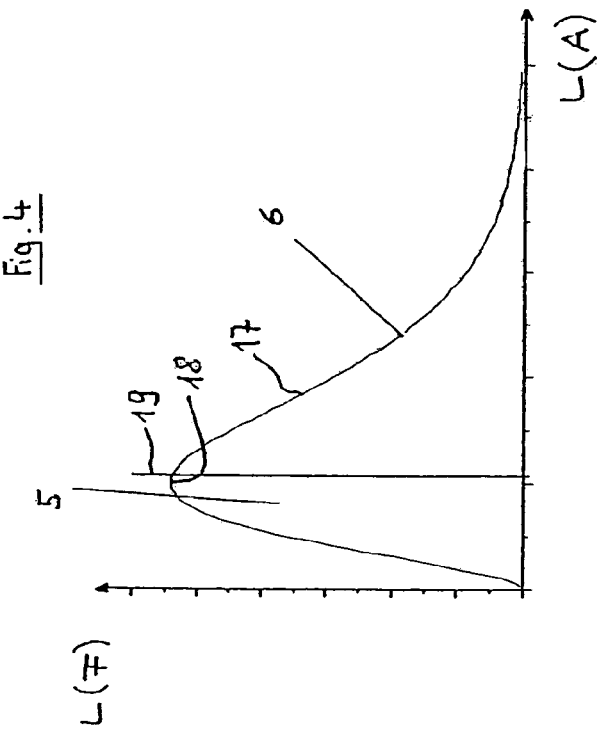

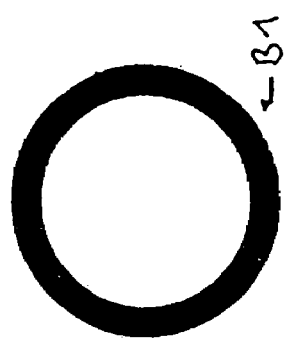
Fig. 6a
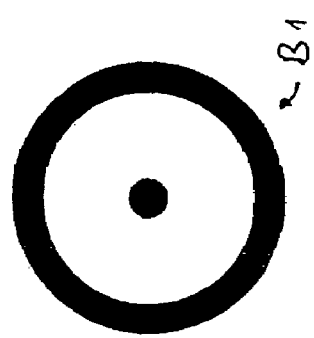
Fig. 6b
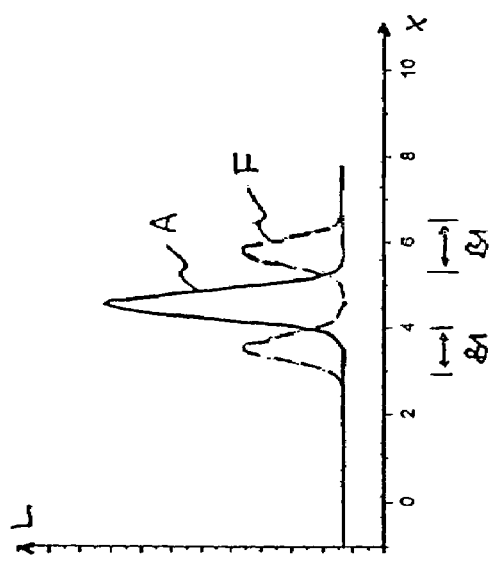
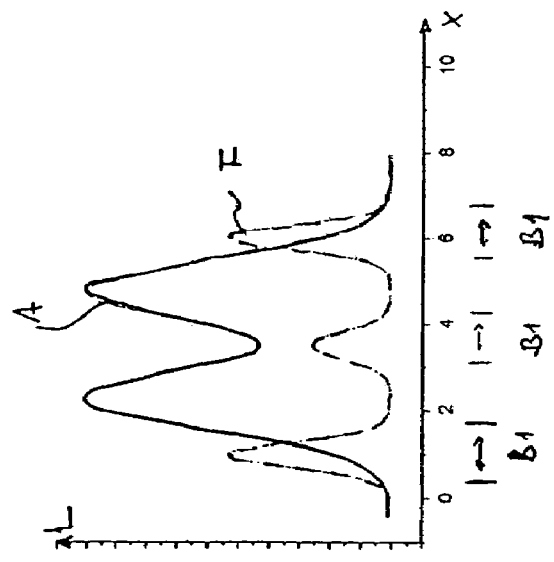

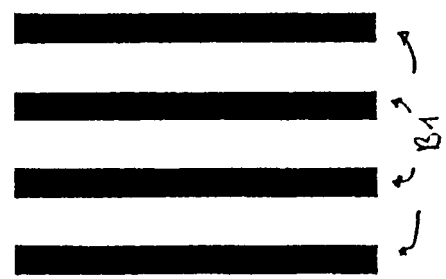
Fig. 8a
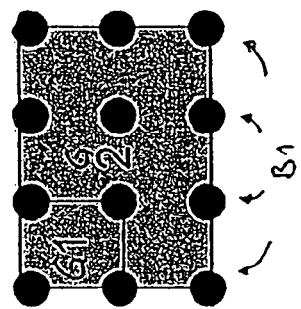
Fig. 8b
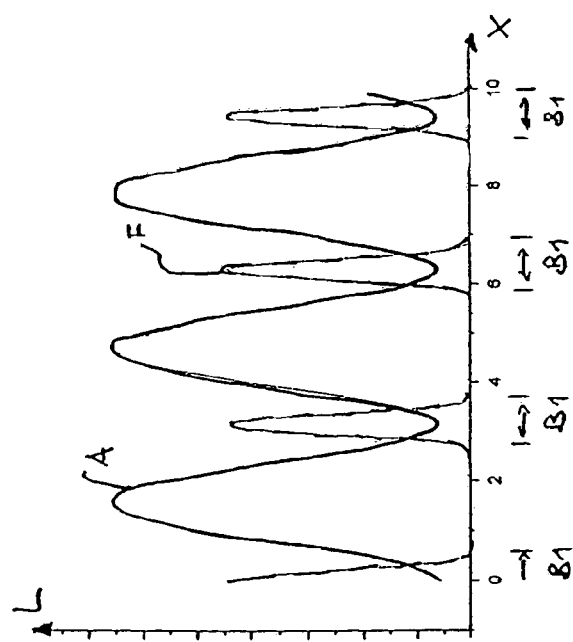
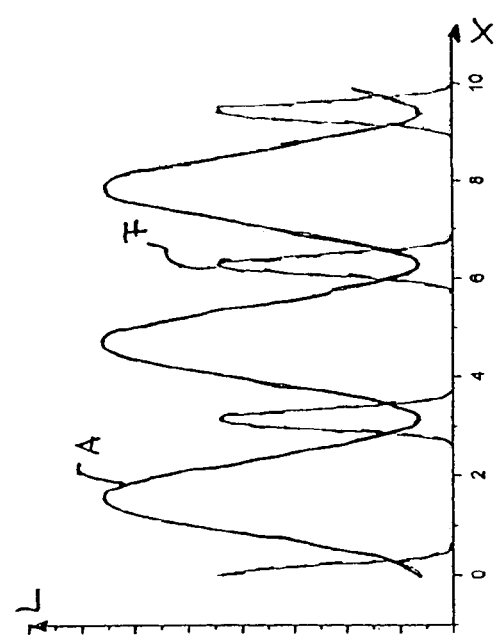

US 7,485,875 B2

RESOLUTION-ENHANCED LUMINESCENCE MICROSCOPY

RELATED APPLICATIONS

The current application claims the benefit of priority to German Patent Application No. 10 2005 034 443.7 filed on Jul. 22, 2005 and to U.S. Provisional Patent Application No. 60/702,342, filed on Jul. 25, 2005. Said applications are incorporated by reference herein.

FIELD OF THE INVENTION

The invention relates to resolution-enhanced luminescence microscopy and, in particular, to a method wherein a luminescent sample to be examined is illuminated with exciting radiation and an image of the sample excited to luminescence is obtained. The invention further relates to a microscope for resolution-enhanced luminescence microscopy of a sample, said microscope comprising means for excitation of luminescence which irradiate the sample with exciting radiation, and means for obtaining an image of the excited sample.

BACKGROUND OF THE INVENTION

A classic field of application of light microscopy for examining biological preparations is that of luminescence microscopy. This involves the use of certain dyes (known as phosphores or fluorophores) for specific marking of samples, e.g. of cell components. As mentioned above, the sample is illuminated with exciting radiation and the luminescence light excited thereby is detected by suitable detectors. For this purpose, a dichroic beam splitter is usually provided in the light microscope in combination with block filters which split off fluorescence radiation from the exciting radiation and enable separate observation. This approach enables the imaging of individual, differently dyed cell components through the light microscope. Of course, it is also possible to dye several portions of a preparation simultaneously with different dyes specifically depositing on different structures of the preparation. This method is referred to as multiple luminescence. It is also possible to measure samples which luminesce per se, i.e. without addition of dyes.

As is common practice, luminescence is understood herein to be the general term for phosphorescence and fluorescence, thus covering both processes.

It is further known in the examination of samples to use laser scanning microscopes (also abbreviated as LSM) which, by means of a confocal detection arrangement (this is then referred to as confocal LSM) or by non-linear sample interaction (known as multi-photon microscopy), image only that plane of a three-dimensionally illuminated image which is located in the focal plane of the objective. An optical cut is obtained, and recording a plurality of optical cuts at different depths of the sample subsequently allows to generate a three-dimensional image of the sample with the help of a suitable data processing device, which image is composed of the various optical cuts. Thus, laser scanning microscopy is suitable to examine thick preparations.

Of course, use is also made of a combination of luminescence microscopy and laser scanning microscopy, wherein a luminescent sample is imaged at various depth levels with the help of an LSM.

Special illumination configurations, such as e.g. a 4Pi-arrangement or arrangements with standing-wave fields, are known for optimal resolution within these limits. Thus, the resolution, in particular in an axial direction, can be considerably improved over a classic LSM. Further, the resolution can be increased to a factor of up to 10 with respect to a diffraction-limited, confocal LSM with the help of non-linear depopulating processes.

FIGS. 1a/b show such a method as described, for example, in U.S. Pat. No. 5,866,911. For resolution enhancement, light radiation having two wavelengths is used. The light radiation of one wavelength is focused onto the sample to be measured as an exciting light beam 1 by means of an objective and excites luminescence, in this case fluorescence, in the sample. For simplification, the representation of FIGS. 1a/b only shows the one-dimensional case. The enhancement in spatial resolution is then effected in that a light beam 2 having a different wavelength depopulates partial areas of the fluorescent state excited by the exciting light beam. Therefore, this light beam is also referred to as "quenching radiation". For example, irradiation is then effected such that the main maximum of the quenching light beam 2 and the main maximum of the exciting light beam 1 partially overlap, as is clearly recognizable in FIG. 1a. Due to this "depletion" of the sample at the edges of the area illuminated by exciting radiation 1, only a reduced volume 3 still emits fluorescence, as is clearly visible in FIG. 1b. As a consequence, resolution is enhanced due to this reduction in volume.

FIGS. 2a-c show three possible mechanisms using which such depopulation can be effected. FIG. 2a shows the process of stimulated emission depletion (STED). The exciting radiation is applied to the flourophore of state S1 (arrow A). The depopulation of the thus excited state S1 is effected in the direction of the basic state S0 by light radiation having a wavelength in the range of the fluorescence wavelength. The arrow SE shows this stimulated emission whose wavelength is almost identical with that of the luminescence (arrow F). Thus, the exciting wavelength has a wavelength shorter than the depopulating quenching radiation by the amount of the Stokes shift. Thus, the resolution enhancement according to this approach requires two different sources of light, which is also supported by the prior art constituted by DE 4416558 C2.

FIG. 2b illustrates a further possible process of depopulation for the excited state S1 (arrow A) by effecting excitation up to a still higher state S2 (arrow A+) which can no longer emit luminescence. Such raising is referred to as Excited State Absorption, which is why this approach is also abbreviated as ESA. A corresponding description of this process is found, for example, in U.S. Pat. No. 6,633,432. Since the distances of the energy states in a sample or in a dye, respectively, decrease at higher states, the ESA process uses a light source for depopulation which has less energy and, thus, a longer wavelength than that used for excitation. Accordingly, two different light sources are required again.

A further method of depopulation in the case of fluorescence is known as Reversible Saturable Optical Fluorescence Transition, which is described e.g. in DE 10 325 460 A1 and illustrated in FIG. 2c. For imaging at a high spatial resolution, this approach uses a dye which can be repeatedly switched from a first state 5, in which fluorescence occurs, to a second state 6, in which the dye does not fluoresce, with the help of a switching beam 4, said dye being able to return from the second state 6 to the first state 5, as illustrated in FIG. 2c. Partial areas of the sample with the dye are switched into the second state 6 by the switching beam 4, leaving out a defined area of the sample. Fluorescence light 7 is then excited by an exciting beam 1 and is subsequently recorded. The fluorescence light 7 then only comes from sample volumes which have not been previously irradiated with the switching beam 7. By a suitable overlap of the exciting beam 1 and the switching beam 4, the volume from which the fluorescence light 7 is emitted is smaller than obtainable a priori through the resolution of the exciting beam 1 and the sharpness of the zero of the switching beam 4.

Thus, in all of the three cited methods according to FIGS. 2a to 2c fluorescence is prevented by the use of light radiation having a wavelength not equal to the wavelength for excitation. At the same time, this light radiation has to comprise at least one distinctly limited, local zero of radiation power, which determines the final resolution of the detected fluorescence radiation. When the zero is only provided as a minimum and does not completely vanish, the fluorescence power and, thus, the efficiency of the method will decrease further. This is the case, for example, where aberrations occur in the optical arrangement or in the preparation, respectively.

FIG. 3 shows a known device using one of the three aforementioned methods for resolution enhancement, which is the STED process of the example of FIG. 3. An excitation radiation source 8 generates an Airy distribution in the sample 10, by which the sample is brought from the ground state S0 to the excited state S1. The depopulation of the state S1 is effected by means of a quenching light source 11 which, when a phase plate 12 is used, has a donut-shaped or toroidal spectral composition 13 in the sample 10. The luminescence radiation of the un-depopulated, i.e. undepleted, dye molecules is detected with the help of a detector 14. The depopulation causes the resolution of the microscope to be enhanced beyond the diffraction limit resulting from the Airy distribution. This is shown by a reduced point spread distribution 15 of the high resolution microscope as compared to the conventional microscope 16.

A further method of resolution enhancement is addressed in EP 1 157 297 B1. In said method, non-linear processes are to be utilized by means of structured illumination. As non-linearity, the document mentions the saturation of fluorescence. The described method claims to realize a shift of the object space spectrum relative to the transfer function of the optical system by structured illumination. More specifically, the spectral shift means that object space frequencies V0 are transmitted at a space frequency of V0-Vm, with Vm being the frequency of the structured illumination. At a given space frequency which is the maximum frequency transmissible by the system, this enables the transfer of space frequencies of the object which exceed the maximum frequency of the transfer function by the shifting frequency Vm. This approach requires a reconstruction algorithm for imaging and the evaluation of several photographs for one image.

SUMMARY OF THE INVENTION

Therefore, it is an object of the invention to provide a luminescence microscopy method or a luminescence microscope, respectively, which achieves resolution enhancement without resorting to several wavelengths or without complex image reconstruction algorithms, respectively.

According to the invention, this object is achieved by a resolution-enhanced luminescence microscopy method, wherein a sample is excited by irradiation of exciting radiation so as to emit a determined luminescence radiation, and an image of the luminescent sample is obtained, which luminescent sample is transferable from a first state of luminescence, in which first state the sample's excitability for emission of the determined luminescence radiation increases up to a maximum value as the exciting radiation power increases, to a second state of luminescence, in which second state the sample has reduced excitability for emission of the determined luminescence radiation as compared to the first state, wherein the maximum value of the luminescence radiation is assigned to a threshold value for the exciting radiation power, the sample is transferable into the second state by irradiation of exciting radiation power above the threshold value, wherein partial areas of the sample are brought into the first state and adjacent partial areas of the sample are brought into the second state by irradiating exciting radiation with an exciting radiation distribution having at least one spatial power maximum above the threshold value and at least one spatial, local power minimum below the threshold value, wherein the image of the luminescent sample comprises sample areas being in the first state and sample areas in the second state, with sample areas being in the first state predominantly contributing to the image of the luminescent sample and the image thereby having enhanced spatial resolution with respect to the exciting radiation distribution.

The object is further achieved by a microscope for resolution-enhanced luminescence microscopy, said microscope comprising means for exciting luminescence which means irradiate exciting radiation onto the sample and, thus, excite the emission of determined luminescence radiation in the sample, means for obtaining an image of the luminescent sample, wherein the means for excitation irradiate the exciting radiation with a determined exciting radiation distribution having at least one spatial power maximum, which is located above a threshold value, and at least one spatial, local power minimum, which is located below the threshold value, said threshold value separating two luminescence regions of the sample—a first-state region present at exciting radiation powers below the threshold value, in which region the excitability for emission of the determined luminescence radiation increases as the exciting radiation power increases, up to a maximum value which is achieved at the threshold value, and a second-state region during and/or after exciting radiation powers above the threshold value, in which region the sample has a reduced excitability for emission of the determined luminescence radiation, and wherein the imaging means detect sample areas in the first region, which have been irradiated with exciting radiation power below the threshold value, and sample areas in the second region, which have been irradiated with exciting radiation power above the threshold value, with sample areas in the first region predominantly contributing to the image of the sample and the image thereby having an enhanced spatial resolution with respect to the exciting radiation distribution.

Thus, a sample is used or the microscope is designed for a corresponding sample, respectively, whose luminescent material substantially has one of two states. In a first state, which appears when exciting radiation power below the threshold value is irradiated and which is achieved by the means for excitation, the material emits luminescence radiation, whose power usually increases as the exciting radiation power increases. In a second state, which is present when exciting radiation power above the threshold value is irradiated, there is either no luminescence or reduced luminescence. Also, absorption properties changed with respect to the first state and/or luminescence radiation emission having other optical properties than in the first state, e.g. with a different spectral composition, polarization or duration, can occur. With respect to the sample which is, of course, composed of a multiplicity of fluorescent or auto-fluorescent molecules, two regions of different states result. In a first state region, the majority of the molecules is in the first state; in a second state region, the majority is in the second state. Now, according to the invention, sample areas are brought into the first state region (or state, in short) and other sample areas are brought into the second state region (or state, in short). The spatial proximity of the areas which have been brought into the first state, i.e. on which exciting radiation power below the threshold value is incident, and areas in the second state, i.e. areas being irradiated with exciting radiation power above the threshold value, generates a significant resolution enhancement as compared to the exciting radiation distribution.

Thus, the technical solution according to the invention achieves said resolution enhancement by a non-linear characteristic curve of luminescence, which curve describes the emitted luminescence radiation as a function of the exciting radiation power and has a local maximum. It is advantageous, but not stringently required, that the characteristic curve has relatively steep slopes on both sides of said maximum. A multi-photon process may also be employed for excitation.

Since in the approach according to the invention sample areas in the first state contribute luminescence radiation to the image, if possible exclusively, and sample areas in the second state luminesce at least to a lesser extent, resolution enhancement is achieved, because the sample image shows a structure going beyond the structure of the exciting radiation distribution. This intensity structure is the more distinct, the more clearly the emission power differs between the first and second states.

By irradiation of the exciting power above the threshold value corresponding to the maximum of the characteristic curve of fluorescence, less fluorescence is excited than in the first state. For this purpose, the exciting radiation distribution is provided with powers above the threshold value in the microscope. Radiation at a different wavelength, as previously required in the prior art, is no longer needed. The microscope according to the invention or a device for carrying out the method according to the invention are, thus, much simpler, in particular requiring only one single light source whose resolution affects image quality. Also, the chromatic requirements with respect to the exciting radiation are considerably simplified as compared to the prior art, because it is no longer required to cover a relatively wide wavelength range.

The microscope is adapted to the sample, because the irradiated exciting radiation distribution takes the threshold value into consideration for transmission.

Moreover, the approach according to the invention does not stringently require the sample areas illuminated with exciting radiation power above the threshold value to be "normally" excited before (as is required, for example, in the STED approach or in the ESA approach), if a sample is used which shows considerably reduced or even disappearing excitability, either permanently or for a certain period of time, after irradiation with exciting radiation power above the threshold value.

It is preferred to use a sample or dye, respectively, which does not luminesce at an exciting radiation power above the threshold value, emits luminescence radiation with other properties than the given luminescence radiation and/or has modified absorption properties for exciting radiation which lead to reduced luminescence.

Thus, according to the invention, resolution enhancement is achieved in that only little, if any, luminescence radiation from sample areas illuminated with exciting radiation intensity above the threshold value contributes to imaging. Depending on the luminescence property which the sample has in the second state, i.e. during and/or after exciting radiation power exceeding the threshold value, this reduced contribution to the image is effected in different ways. If the sample no longer shows any luminescence at all, luminescence radiation is no longer detected either. If, on the other hand, the sample shows luminescence radiation with modified optical properties in the second state, corresponding optical filtering, e.g. with respect to the spectral composition or the polarization, will be effected for blocking. If modified life times of the excited luminescence states appear, temporal filtering will achieve blocking.

In order to further limit the sample areas in the first state or to select some of these sample areas, respectively, it is preferred to effect confocal detection. Due to the inventive reduction of the volume excited to luminescence below the diffraction limit, spatial resolution exceeding that of normal confocal detection is thus achieved.

It is essential that not all of the areas illuminated with exciting radiation contribute to the luminescence image, but that sample areas illuminated with exciting radiation power exceeding the threshold value are contained in the image, if at all, only to a reduced extent, which automatically results in the resolution enhancement with respect to the irradiation of exciting radiation, because a spatial reduction of the luminescent sample volume relative to the excited sample volume is achieved. Optical structures are present in the image which were not present in the exciting radiation distribution. Thus, the resolution of the image is enhanced beyond the resolution of the exciting radiation coupled in.

Particularly advantageously, use is made of a sample or of dyes or the microscope is adapted to dyes which can be reset again from the second state to the first (original) state by irradiation of resetting radiation which has different optical properties than the exciting radiation. The microscope then comprises suitable means for this purpose. This means that the second state is an at least largely reversible state. Areas blocked out from the luminescence image by irradiation of exciting radiation power above the threshold value can then be excited to luminesce normally again in the first state after irradiation of the resetting radiation. A method improved in this way or a microscope embodied in this way is then suitable for applications wherein different areas of a sample are to be imaged several times. Therefore, it is preferred for such applications to use a sample or a dye showing reduced sensitivity for exciting radiation in the second state, i.e. after illumination with exciting radiation above the threshold value, the reduction in sensitivity being at least partially reversed (and the first state being restored) by irradiation of a resetting radiation having optical properties which differ from the exciting radiation. At least those areas of the sample illuminated with exciting radiation power exceeding the threshold value are irradiated with resetting radiation. In this case, it is important that the resetting radiation, which returns the sample to the first state, does not contribute to achieving the resolution enhancement and can thus also be coupled into the sample in a very roughly structured manner at best.

In a particularly advantageous further embodiment of the invention, the sample which can be returned to the first state again with respect to its luminescence properties allows imaging by scanning. In doing so, the sample may be scanned, e.g. by a scanning unit, using a spot, line or multi-spot area, for example. Resetting radiation is then respectively irradiated between two scanning steps in order to enable renewed irradiation of exciting radiation below and above the threshold value in the new scanning step. Thus, enhanced resolution is achieved in each scanning step, which provides an image with considerably enhanced resolution on the whole.

Accordingly, irradiation of the exciting radiation distribution generates a spatial structure for fluorescence radiation. In most cases, said structure is symmetrical with respect to the exciting radiation distribution. If a certain fluorescent surface shape, e.g. a point, is desired, parts of the fluorescent sample are preferably blocked out. This is possible without affecting the resolution of the desired surface shape, because sufficient gaps between adjacent fluorescent areas can be ensured.

In principle, two variants are possible for excitation of the sample above or below the threshold value. In a first variant, principally diffraction-limited illumination is effected which may be point-shaped, radially symmetrical or may have a central maximum, like the known Airy function, although this is not required. In this form of excitation distribution, the exciting radiation distribution is preferably diffraction-limited.

In the case of diffraction-limited exciting radiation distribution, a toroidal distribution may be particularly advantageously used, which has an exciting radiation power above the threshold value in the core area of the toroidal distribution and below the threshold value in peripheral areas. At the center circumscribed by the torus, a point-shaped luminescence distribution is then obtained which is considerably smaller than a diffraction-limited Airy disk would be. Of course, since sample areas located at the outer periphery of the torus are also illuminated with exciting radiation power below the threshold value, for the above-mentioned reasons of symmetry, luminescence radiation is also excited there. In order to generate a point-shaped fluorescence image, it is convenient to block out these areas, e.g. with the help of confocal detection, which merely allows luminescence radiation to pass which is generated in the center circumscribed by the torus. However, the luminescent center is nevertheless smaller than the (diffraction-limited) resolution of confocal detection per se allows. Of course, blocking out can also be achieved in other ways. For example, with respect to the excitability of luminescence, outer areas can be selectively deactivated or the circumscribed center can be selectively activated. Thus, the method or the microscope of the invention allows a resolution beyond the physical diffraction limit while at the same time influencing the shape of the fluorescent area.

In a second variant, planar structured illumination is employed, wherein the area may also be provided as one or more line(s), diffraction-limited in one direction. Partial areas of the illuminated area have an exciting radiation power above the threshold value and other partial areas have an exciting radiation power below the threshold value. Such planar illumination allows particularly quick raster-scanning of a large sample. Of course, the same also applies to a multi-spot arrangement, wherein a plurality of diffraction-limited illumination spots are incident on the sample, which are spaced apart from each other by a distance allowing them to be detected clearly separated from each other. For planar structured sample illumination, a line or cross grid is suitable.

Depending on the sample, sample areas may still show a certain residual luminescence in the second state. This may either be caused by the sample itself or by migrations of luminescent material between the differently illuminated sample areas, for example by diffusion. The sample itself may, for example, have interfering auto-fluorescence or may contain dyes which cannot be brought into a second, reversible state. As a result, there is residual luminescence radiation in areas which have been illuminated with exciting radiation power above the threshold value. This residual luminescence may be suppressed generally by using a suitable threshold value during detection.

The use of a lock-in technique known per se suppresses this background radiation while the image signal is improved. For this purpose, one will intensity-modulate the exciting radiation according to a reference frequency, either in sample areas to be brought into the second state or in sample areas remaining in the first state, and consider this reference frequency during detection of the luminescence radiation by way of the lock-in technique. For this purpose, the microscope comprises a modulator and a lock-in amplifier arranged following the luminescence detector. Said amplifier then separates the modulated signals and suppresses the unmodulated signals, which enables high resolution detection also without a decrease in the peak level of the useful signal in case of the above-mentioned residual luminescence. The modulated signals thereby fully contribute to the high resolution image.

An alternative method of suppressing residual luminescence is a subtraction method, in which two images are subtracted from each other. A first image is recorded with exciting radiation power below the threshold value; a second image is recorded with exciting radiation power above the threshold value. The difference between the two images separates the residual luminescence. Other possible approaches for suppressing residual luminescence use further properties of samples or dyes used in variants of the invention, e.g. the evaluation of different luminescence lifetimes in the first and second states, respectively, the use of different optical properties of the luminescence radiation in the first or second state, or the like.

Further, parts of the sample located outside the focal plane to be detected are blocked out in advantageous embodiments in order to increase the focal depth. Axial resolution is thereby uncoupled from lateral resolution at the same time. For this purpose, the sample is first brought into the second state and is then reset only in the focal plane. The same is achieved by a corresponding depth structure of the exciting radiation intensity with a minimum in the focal plane. For this purpose, an arrangement according to the principles of DE 102 57 423 A1 can be suitably modified.

In advantageous embodiments, the above-mentioned microscope according to the invention realizes one or more of the above-mentioned further embodiments. Since the exciting radiation is used both to excite luminescence and to prevent or reduce luminescence, it is advantageously possible to provide one single source of exciting radiation emitting exciting radiation and following which there is arranged a unit which imposes a minimum, preferably of variable depth, on the beam profile, the power in the minimum being below the threshold value.

DESCRIPTION OF THE DRAWINGS

The invention will be explained in more detail below by way of example and with reference to the drawings, wherein:

FIGS. 2a-2c show schematic drawings of various prior art methods for resolution enhancement;

FIG. 3 shows a resolution-enhanced fluorescence microscope of the prior art;

FIG. 4 shows a characteristic curve of fluorescence of a sample;

FIG. 5 shows a schematic drawing concerning the resolution enhancement according to the invention;

FIGS. 6a/b show one- or two-dimensional power distributions as they appear in the case of a resolution enhancement according to a first and second form of method;

FIGS. 8a/b show representations of fourth and fifth forms of methods similar to FIGS. 6a/b;

DETAILED DESCRIPTION OF PREFERRED EMBODIMENTS

Figure 1B:
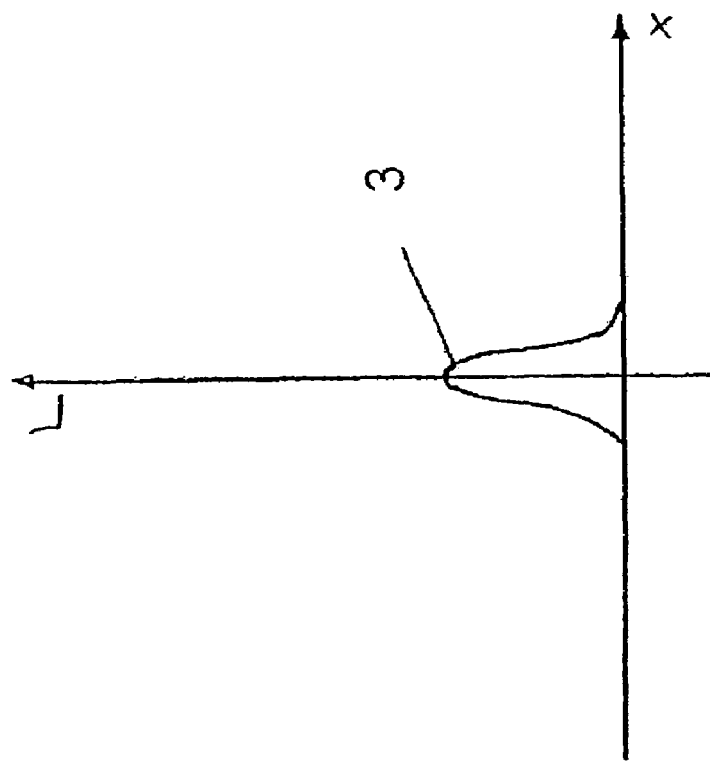
FIGS. 1a and 1b show locally varying power distributions for prior art methods.
Figure 1A:
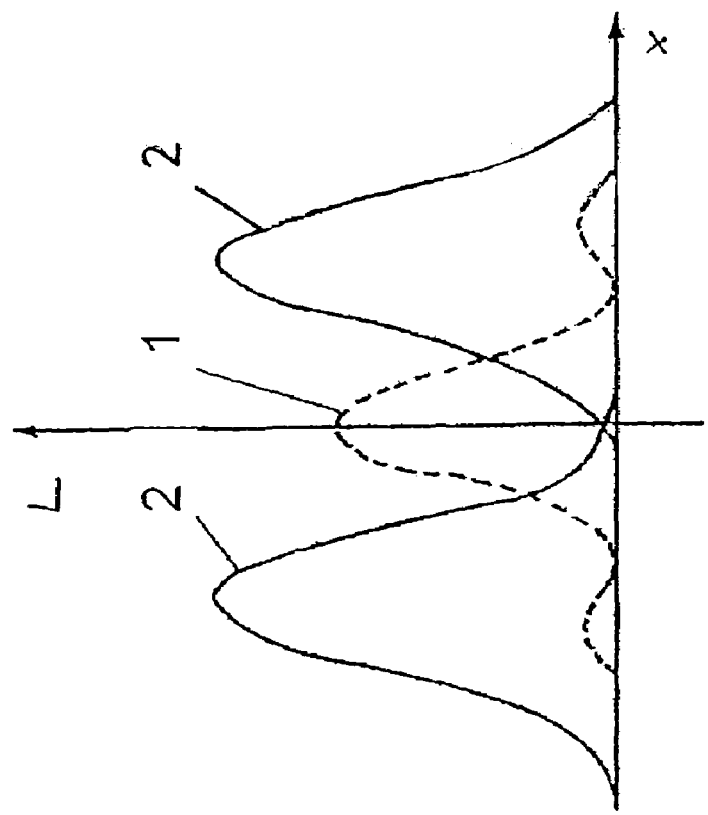

In the following, various embodiments concerning resolution-enhanced luminescence microscopy will be illustrated by explanations relating to processes and by microscope descriptions. This is done purely by way of example with reference to various fluorescence microscopes and methods of fluorescence microscopy. Of course, the exemplary embodiments described hereinafter, i.e. forms of methods and microscopes, can also be used for substances having a different kind of luminescence, e.g. for phosphorescent samples or dyes. Any reference made hereinafter to a dye should also be construed merely as an example. Instead of a dye which may be used to prepare a sample, a directly fluorescent (or phosphorescent) substance may also be present, of course, as the sample, so that addition of a dye can be dispensed with. Also, additional dyes can be used which show different properties and cannot be brought into a second state. Further, features described for individual forms of methods or microscopes can also be used for other described forms of methods or microscopes, so that combinations not set forth herein are also possible.

By way of example, FIG. 4 shows a characteristic curve of fluorescence 17 for a dye used for the invention. In this characteristic curve of fluorescence 17, the power L of the emitted fluorescence radiation F is plotted against the power L of the exciting radiation A. As can be seen, the characteristic curve 17 rises in a largely linear, definitely monotonous manner, up to a maximum 18 and then drops again above a threshold value 19 for the exciting radiation power. Two regions of different states are recognizable, which are located to the left and to the right of the threshold value 19 or the maximum 18, respectively. If an exciting radiation power being below the threshold value 19 is irradiated, the dye is primarily in a first state 5. In this case, it can emit fluorescence radiation. If the exciting radiation power is increased to above the threshold value 19, no transition of the dye molecules to a second state 6 takes place. Dye molecules in the second state 6 are then either not fluorescent, emit fluorescence radiation with modified optical properties and/or possess a modified absorption property with respect to the first state 5. The modified optical properties for fluorescence emission or absorption can relate to the spectral composition, the polarization and/or the life time of the fluorescence radiation. As a result, the power of the fluorescence radiation F decreases again, if reference is made to the type of fluorescence radiation emitted in the first state 5.

The invention now uses the characteristic curve 17 such that irradiation of the exciting radiation A only brings part of the sample into the first state region (or, in short, the first state) 5, while it brings another part of the sample into the second state region (or, in short, the second state) 6. Thus, areas illuminated with exciting radiation power above the threshold value 19 emit the determined fluorescence radiation only to a reduced extent. The second state 6 is advantageously a reversible state. This means that at least after a certain time or after active influence, a dye once irradiated with exciting radiation power above the threshold value 19 shows the properties of the first state 5 again. An example of a dye for which the inventors recognized a characteristic curve according to FIG. 4 is the substance referred to as Dronpa, which is described in the publication of R. Ando et al., "Regulated fast nucleocytoplasmic shuttling observed by reversible protein highlighting", Science, Nov. 19, 2004, Vol. 306, p. 1370-1373. The dye is available from Amalgaam, Woburn, Mass., USA, under the name of Dronpa-Green, Code-No. AM-V0071, and has been known in connection with fluorescence marking of molecules whose properties of transport through cell membranes are to be examined. The Dronpa dye can be excited at a wavelength of 488 nm and can be returned to the first state 5 again after excitation to the second state 6 by radiation at a wavelength of 405 nm.

In combination with a suitable exciting radiation distribution during illumination of the sample, the use of the dye having the characteristic curve of FIG. 4 or a similar characteristic curve leads to a considerable resolution enhancement. In contrast to the prior art, radiation of only one wavelength is irradiated, and only this radiation contributes to resolution. In those embodiments where the dye does not spontaneously return to the first state 5, resetting can be achieved by irradiation of a resetting radiation R, which, however, does not contribute to resolution enhancement.

With the exciting radiation A, not only excitation of the dye molecules from the ground state to the first excited state (first state 5) is achieved, but fluorescence or even depopulation (second state 6) is prevented as well. During depopulation, the dye molecules transit from the first state to the second state. Both states have different optical fluorescence properties. After excitation with the exciting radiation A, the high resolution fluorescence image can be obtained at once, with high resolution referring to the optical resolution of the exciting radiation A. If the dye does not spontaneously return from the second state to the first state, resetting is effected actively, for example by means of resetting radiation R which has optical properties differing from those of the exciting radiation A.

Initially, for example, the sample P to be examined is in the first state 5, in which the power of the fluorescence radiation F increases as the power of the exciting radiation A increases. Now, irradiation of the exciting radiation A is effected such that the exciting radiation power is above the threshold value 19 in some sample areas B2. In other areas B1, it is below said value. Thus, some of the sample areas are in the first state 5, others are in the second state 6, depending on whether the power of the exciting radiation is above or below the threshold value 19. FIG. 5 schematically shows the transition of the sample by irradiation of exciting radiation A into sample areas B1 in the first state 5 (right-hand part of the lower half of FIG. 5) as well as sample areas B2 in the second state 6 (left-hand part). Sample areas B2 in the second state 6 can no longer fluoresce efficiently, in particular if exciting radiation power clearly above the threshold value 19 was used. The term "fluorescing" relates to fluorescence radiation having certain properties. Thus, it is quite possible that fluorescence radiation is emitted also in the second state 6, but with other properties than in the first state 5. Thus, either the absorption properties and/or the fluorescence properties of the sample are changed in the second state.

Areas B1 of the sample which remain in the first state 5 continue to emit the same fluorescence radiation F after irradiation of exciting radiation A. Irradiation of resetting radiation R (FIG. 5 illustrates this process by a corresponding arrow) brings the entire sample P back to the first state 5, thus reversing the division into two differently fluorescing sample areas B1 and B2.

The division of the sample into sample areas B1 which are in the first state 5 and sample areas B2 which are in the second state 6 now allows emission of fluorescence radiation F to be limited to a volume of the sample P which is smaller than the volume initially illuminated with exciting radiation A. Thus, in the fluorescent image a structure can be obtained that was initially not present in the exciting radiation distribution. The reason for this is the skillfully used non-linearity of the characteristic curve 17.

FIGS. 6a and 6b show two forms of methods illustrating what the exciting radiation distribution for resolution enhancement can look like. The left-hand side of both Figures shows a one-dimensional sectional view of exciting radiation distribution and fluorescence radiation distribution, respectively. Each respective right-hand side shows a top view of the two-dimensional image of the fluorescence radiation distribution.

In FIG. 6a, a point-shapedly distributed exciting radiation A is irradiated. In this case, the distribution is a diffraction-limited Airy distribution. This results in excitation of fluorescence radiation F with an ellipsoidal, donut-shaped distribution in the dye, which distribution appears in the two-dimensional image as a laterally fluorescent, circular ring. Only the sample areas B1 fluoresce. A fluorescent ellipsoidal ring extends axially. This sample area B1 is smaller than the diffraction limit of the exciting radiation allows.

If, however, an also diffraction-limited, donut-shaped distribution of the exciting radiation A is irradiated, a radiating sample area B1 will result, which corresponds to a decreased Airy distribution surrounded by a ring-shaped fluorescent area. Therefore, in the sectional view three peaks appear as sample areas B1 in the distribution of the fluorescence radiation F. In this case, the point-spread distribution 16 is also smaller than the diffraction limit allows. Resolution enhancement via normal point-spread distribution depends essentially on the combination of the characteristic curve 17 and the power distribution of the exciting radiation A.

Figure 7:
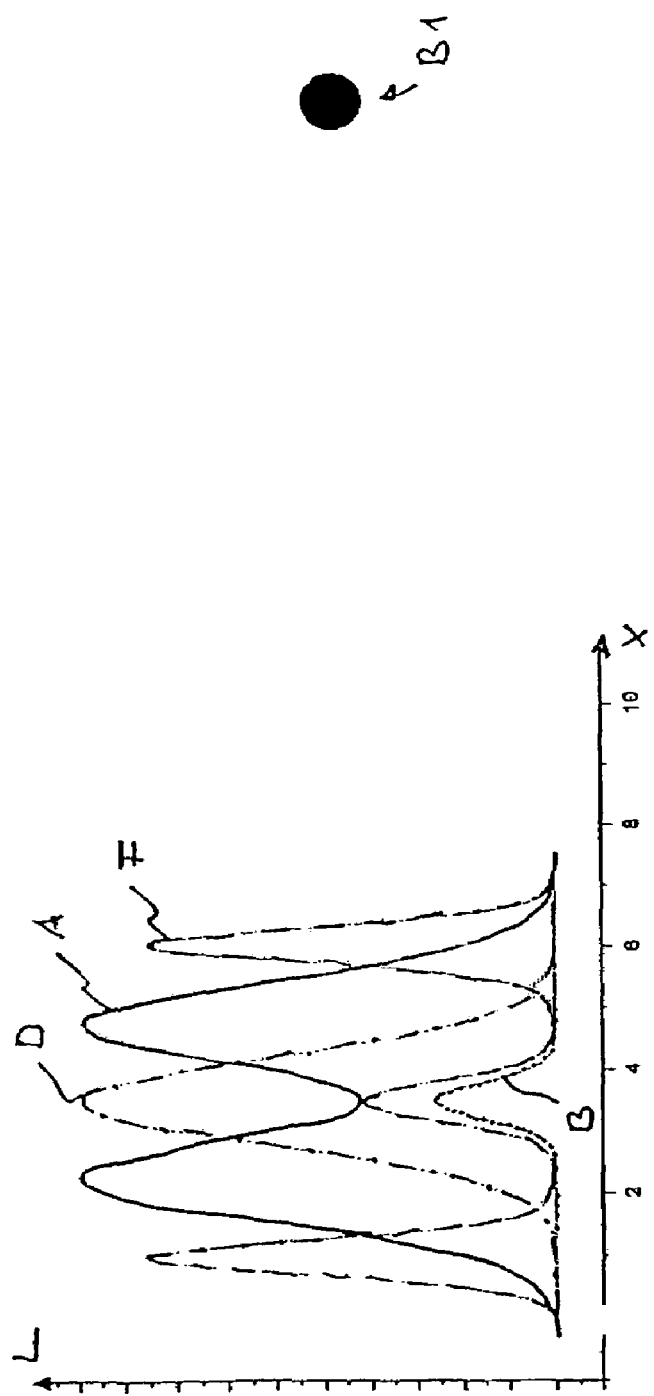
FIG. 7 shows a representation of a third form of method similar to FIGS. 6a/b.

In order to block out the ring-shaped outer area, it is additionally possible to effect confocal detection which selects the mean peak by suitable adjustment of a confocal detection volume D. This is schematically shown as the third form of method in FIG. 7. The fluorescent sample area B1 still detected then consists of the mean peak. On the whole, for example, an imaging volume B (dotted line in the right-hand illustration of FIG. 7) is achieved which is 2.5 times narrower than the conventional point-spread distribution and even 1.7 times narrower than a confocal point-spread distribution. In the case of a donut-shaped excitation distribution as shown in the right-hand illustration of FIGS. 6b and 7, respectively, the resulting distribution of the imaging volume B or of the mean peak, respectively, of the point-spread distribution of FIG. 6b is radially symmetrical. If two illumination spots are used, a maximum resolution enhancement is achieved along the connecting line of the spot maxima.

Alternatively, the outer fluorescent ring in FIG. 6b is blocked out by selective resetting of the dye from the second state 6 to the first state 5 in the area of the confocal detection volume D. The procedure/principle is then as follows: First, excitation is effected with exciting radiation such that the sample portion to be examined completely reaches the second state. Next, resetting radiation R having a distribution which corresponds to the confocal detection volume D is irradiated, thereby resetting part of the sample. Upon another excitation with the exciting radiation distribution A according to FIG. 7, only the imaging area B located within this sample portion reaches the first state and emits fluorescence radiation F in the form of the mean peak, such as it also remains in the variant of FIG. 7. The ring-shaped outer area remains in the second state and does not fluoresce.

In a fourth form of method, structured planar illumination is effected as shown, for example, in FIG. 8a. Exciting radiation A which is sinusoidally distributed in the x direction leads to fluorescence radiation F in the troughs of the sinusoidal power distribution. The fluorescent sample areas B1 are strip-shaped. However, the strips are considerably narrower than the strips of the sinusoidal distribution of the exciting radiation A. It is advantageous that the sinusoidal distribution of the exciting radiation A does not have, or is not required to have, zeros as minima. Although the height of the resulting distribution of the fluorescence radiation F depends on the power of the excitation minima, its width does not. Thus, the depth of the minima of the sinusoidal exciting radiation distribution is uncritical for the width of the strips and, thus, for resolution. In the exemplified case, the period of the sinusoidal strip distribution of the exciting radiation A is set to the limit frequency of resolution. As detector a matrix detector is used for example. The strip width and, thus, the resolution is improved by a factor of 6 over the limit frequency of resolution. A high resolution full image is then obtained by shifting the strip pattern.

Alternatively, instead of strip-shaped wide-field illumination, focal line-shaped illumination can be used, with the line being modulated along its longitudinal axis (e.g. sinusoidally) such that in some line segments the power is located above the threshold value and in other line segments below the threshold value. The scanning movement is effected perpendicular to the line and along the line. The detector is a suitable high resolution line detector.

FIG. 8b shows a further embodiment based on the fourth form of method of FIG. 8a. In this fifth form of method, structuring of the distribution of the exciting radiation A is effected in both lateral axes, i.e. in the sample plane, such that a matrix-shaped illumination spot distribution is given. This is one-dimensionally illustrated in the sectional view in the left half of FIG. 8b. A matrix of bright excitation spots is imaged on the sample perpendicular to the optical axis. Each illumination spot now has a detector assigned to it. A displacement of the spot pattern relative to the sample allows to measure in gaps between the spots as well. The area in which the displacement of the matrix-shaped pattern has to be effected is shown as area G1 in FIG. 8b. By raster-scanning of the spot matrix, for example as known for a conventional laser scanning microscope, the total area G2 is sensed as a whole from individual areas G1. A very high scanning speed is achieved by this parallel approach. At the same time, the resolution is enhanced beyond the exciting radiation distribution as shown by the narrow peaks of the fluorescence radiation F in the sectional view.

Although only lateral resolution has been mentioned so far, axial resolution is also improved for the embodiments.

Figure 9A:
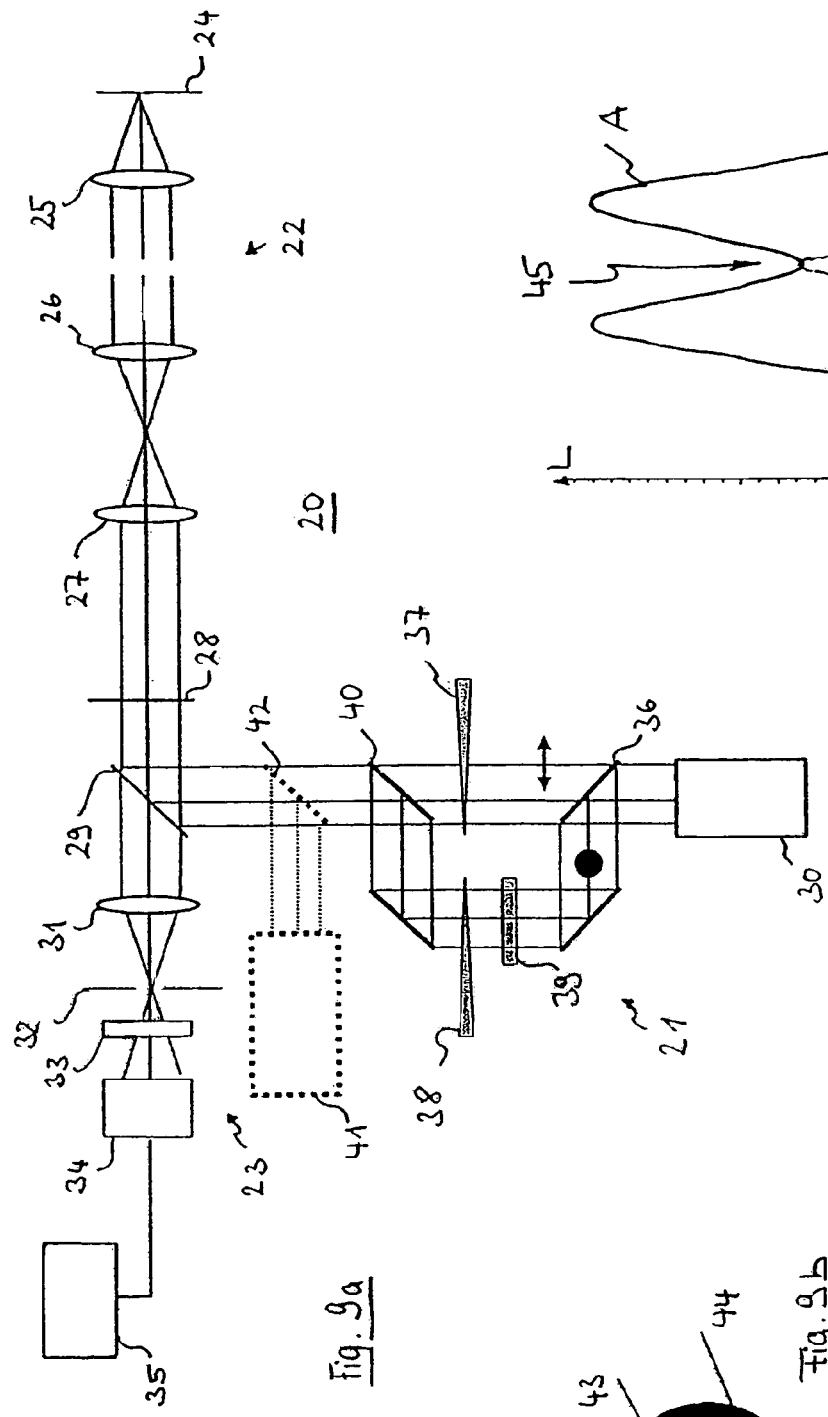
FIGS. 9a/b show a schematic drawing of a first resolution-enhanced microscope.

FIG. 9a shows a laser scanning microscope which can realize each of the explained forms of methods. For forms of methods 1 to 3, the laser scanning microscope 20 is provided, for example, as a single spot-scanning microscope. It comprises an exciting module 21, a microscope module 22 as well as a detector module 23. In the microscope module 22, a sample 24 is located in the focus of an objective 25, preceding which a tube lens 26 is arranged in the direction of illumination. This optical system is preceded by scanning optics 27 which, together with a scanner 28, enable raster-scanning of the sample 24 by shifting the focal point on the sample. A main beam splitter 29 couples the radiation from the exciting radiation module 21 into the microscope module 22 and splits radiation off from the microscope module to the detector module 23, said radiation having been picked up by the sample 24.

The exciting module 21 comprises a light source 30 whose radiation is focused to form the focal point in the sample 24 via the main color splitter 29. The fluorescence radiation F excited in the focal point of the sample 24 is gathered by the objective 25 and coupled out at the main color splitter 29, due to the modified spectral properties as compared to the exciting radiation A, towards a pinhole lens system 31 which is followed by a pinhole 32 as well as a block filter 33 (optional). A spot detector 34 detects the power of the fluorescence radiation F at the focal point. In addition, detection can be effected in a spectrally resolved, polarization-resolved and/or time-resolved manner. The signals from the detector 34 are read out by a control device 35 which controls the operation of the laser scanning microscope 20 as a whole.

Figure 9B:
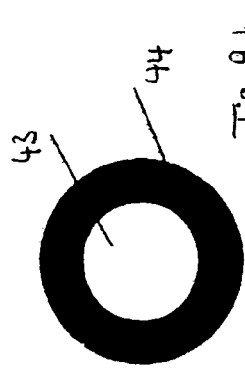

For resolution enhancement, irradiation of the exciting radiation A in the focal point 24 is effected with a given power distribution. In order to predetermine and set the latter, a suitable structure is provided in the exciting module 21. The construction of FIG. 9a comprises a beam splitter 36 which couples out 50% of the radiation power of the light source 30. In the embodiment, the beam splitter 36 is a polarization beam splitter. The partial beams split up in this manner are subsequently superimposed to form a common beam again via a further beam splitter 40, with the intensities and phases of the partial beams being suitably set first. In addition, a phase element 39 is placed in a partial beam, which element can be provided either as a stationary phase element or as a variably adjustable phase element. For example, the phase element 39 has a phase-modifying area 44 as well as a phase-neutral area 49, so that a donut-shaped power distribution is impressed upon the beam. Upon superposition of the two partial beams following the beam splitter 40, exciting radiation A is obtained according to FIG. 10. The structure of the phase element 39 is shown by way of example in FIG. 9b. In order to set the power components of the two partial beams prior to superposition, variable attenuators 37 and 38, respectively, are also placed in each partial beam.

Figure 10:
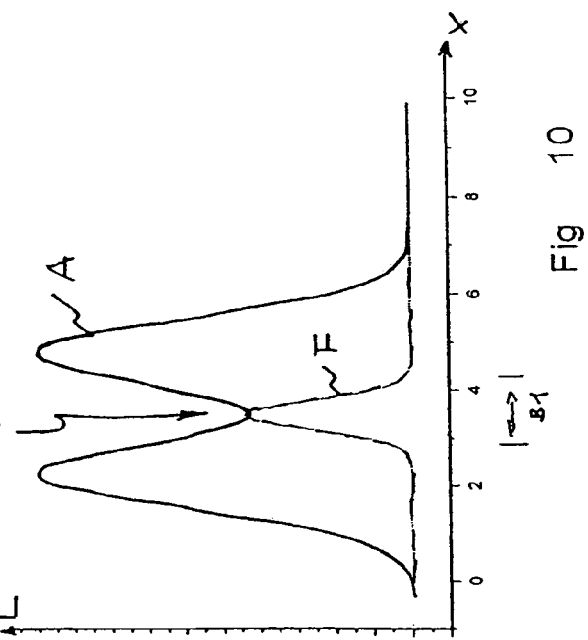
FIG. 10 shows a power distribution similar to FIG. 6a illustrating the operation of the microscope of FIG. 9.

As a result, a power distribution of the exciting radiation A is obtained such as that which is shown in the sectional view of FIG. 10 taken along an x-axis which is perpendicular to the optical axis. The distribution has a minimum 45 whose depth is variably adjustable by setting the attenuators 38 or 37, respectively, i.e. by modifying the relative power of the two partial beams, e.g. by the control device 35. Adaptation of the minimum 45 allows optimal adjustment of the intensity of the fluorescence radiation F also shown in FIG. 10.

The minimum 45 which can be adjusted with respect to its depth can also be generated using a variably adjustable phase element without forming partial beams. For such phase element, a matrix of liquid crystals is suitable, wherein the phase of each individual pixel is adjustable. Of course, other means of generating a donut-shaped radiation distribution with an adjustable minimum 45 are also possible.

For optional resetting of the sample areas B2 from the second state 6 to the first state 5, a resetting radiation source 41 can be provided which is integrated in the exciting beam path of the exciting module 21 via a third splitter 42. However, this construction is optional. Therefore, the illustration in FIG. 9a shows these elements in broken lines. The resetting radiation source 41 is required only if the dye of the sample 24 does not return spontaneously to the first state, but requires active resetting by optical resetting radiation R. However, resetting radiation can also be applied to the sample 24 in other ways, for example by irradiation oblique to the optical axis of the objective 25 with the help of a resetting radiation source attached laterally to the laser scanning microscope.

The microscope of FIG. 9a can carry out the above-described forms of methods. The third form of method requires the use of the pinhole 32 and of the pinhole optics 31 in the detector module 23. If no confocal detection is needed, the components (31, 32) required therefor can be omitted.

Figure 11B:
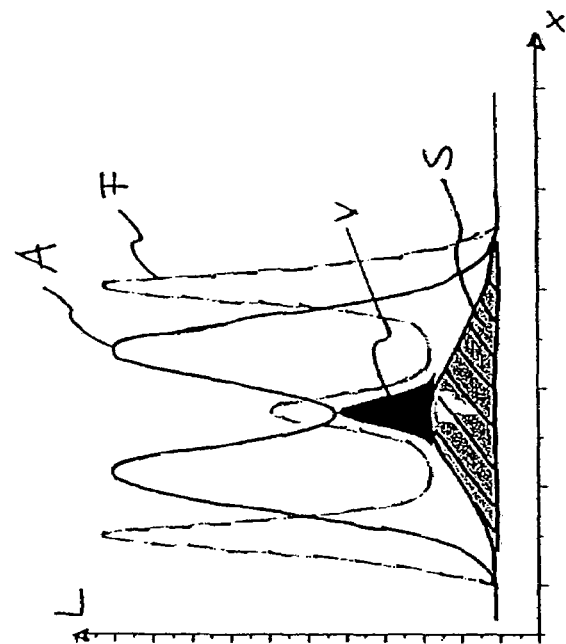
FIGS. 11a/b show a characteristic curve similar to FIG. 4 as well as a power distribution, illustrating a second resolution-enhanced microscope.
Figure 11A:
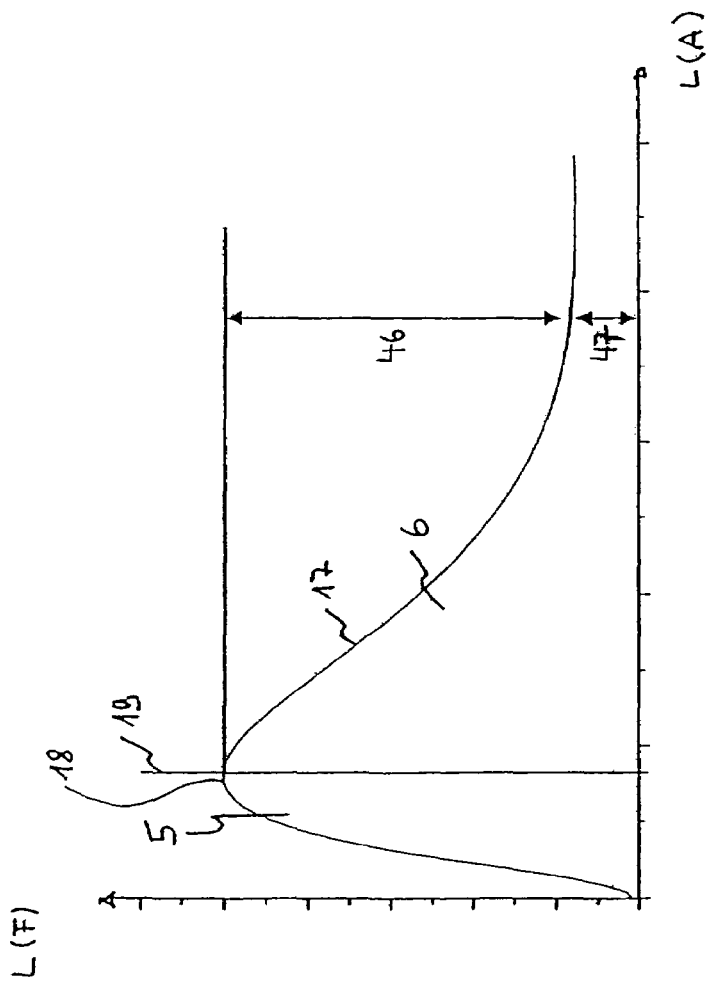

FIG. 11a shows a possibility to further improve the procedure according to the invention. The transition of the sample in the partial area B2 from the first state to the second state 6 may take place in an incomplete manner. This is the case, for example, if the characteristic curve of fluorescence 17 does not fall steeply enough after the maximum value 18, i.e. for powers of the exciting radiation A above the threshold value 19. In the example of FIG. 11a, the characteristic curve 17 does not go back to zero even at high exciting radiation powers. This leads to a residual fluorescence 47 in the sample areas B2 that are in the second state 6, because the reduced portion 46 does not correspond to the maximum value 18. If the fluorescence radiation F were then measured with the microscope of FIG. 9a, for example realizing the third form of method, the imaging volume B would be composed of a low-resolution background S and a high-resolution distribution V. This is schematically illustrated in FIG. 11b, which shows the background S by hatching and the high-resolution distribution V in black.

The same effect may appear if there is a strong diffusion of fluorescent material, for example of the dye molecules. This also results in a residual fluorescence 47 in sample areas B2, although not due to a comparatively weakly falling characteristic curve 17, but due to diffusion of the fluorescent material.

The background S can be suppressed by suitable image recording. A second embodiment of a laser scanning microscope 20 realizing this is shown by way of example in FIG. 12. Any components identical with the construction of FIG. 9a have the same reference numerals so that their repeated explanation is omitted.

Figure 12:
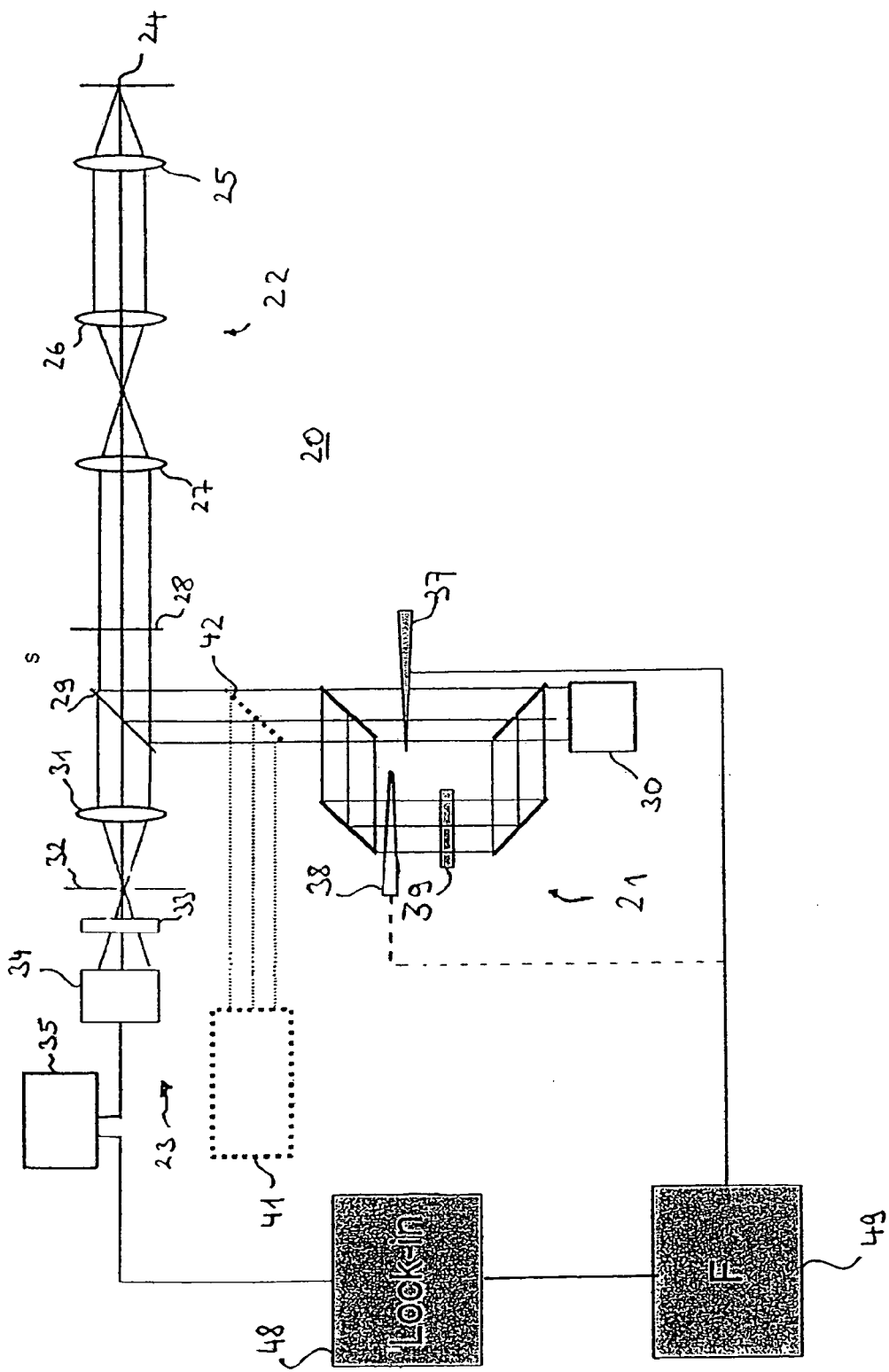
FIG. 12 shows a schematic representation of the second microscope.

In contrast to the construction of FIG. 9a, the detector 34 is now connected to a lock-in amplifier 48, this connection being realized merely by way of example in FIG. 12 via the control device 35. Of course, a direct connection is also possible. Also, the lock-in amplifier 48 can be integrated in the control device 35. The lock-in amplifier 48 is connected to the frequency generator 49 which modulates the minimum 45 in its amplitude. For this purpose, the power of one of the two partial beams is suitably modulated in the exciting module 21. This is effected, for example, by controlling one of the two attenuators 37 or 38. The control line for the attenuator 38 is shown in broken lines in the view of FIG. 12 to indicate this option. Of course, the control of the attenuators can also be effected by the control device 35 which accordingly evaluates the signal from the frequency generator 49. As already mentioned, the lock-in amplifier 48 and/or the frequency generator 49 can be components of the control device 35.

The frequency provided by the frequency generator 49 for modulation of the minimum is also supplied to the lock-in amplifier 48. The signal from the sample areas in the first state 5 is modified by the modulation of the minimum 45, whereas the signals from the background S remain constant. The lock-in amplifier 48 separates the modulated signals and suppresses signals of the background S. This results in separation of the distribution V from the background S, and high-resolution detection is achieved even in case of an incomplete transition to the second state 6.

If the dc portion of the signal is selectively exploited, additional image information which does not have a high resolution is obtained. For example, this image information may relate to differently fluorescing sample areas/sample properties. The high resolution portions and the low resolution portions can be shown superimposed and coded in any form (e.g. color-coded).

As an alternative or in addition to this lock-in detection, it is also possible to record two images. A first image is recorded with an exciting radiation distribution having a minimum 45; the second one is recorded without a minimum 45. For separation of the high resolution distribution V from the background S, the images are then simply subtracted from each other (first image minus second image). The resulting image only contains the information comprising the high resolution distribution V. Further possibilities of suppressing a low resolution background can be the use of different optical properties of the first state 5 and of the second state 6, e.g. if the life times of the two states differ from each other. Also, a different characteristic of the emission spectrum or a characteristic of the absorption spectrum differing between the first state 5 and the second state 6 can be used.

Figure 13:
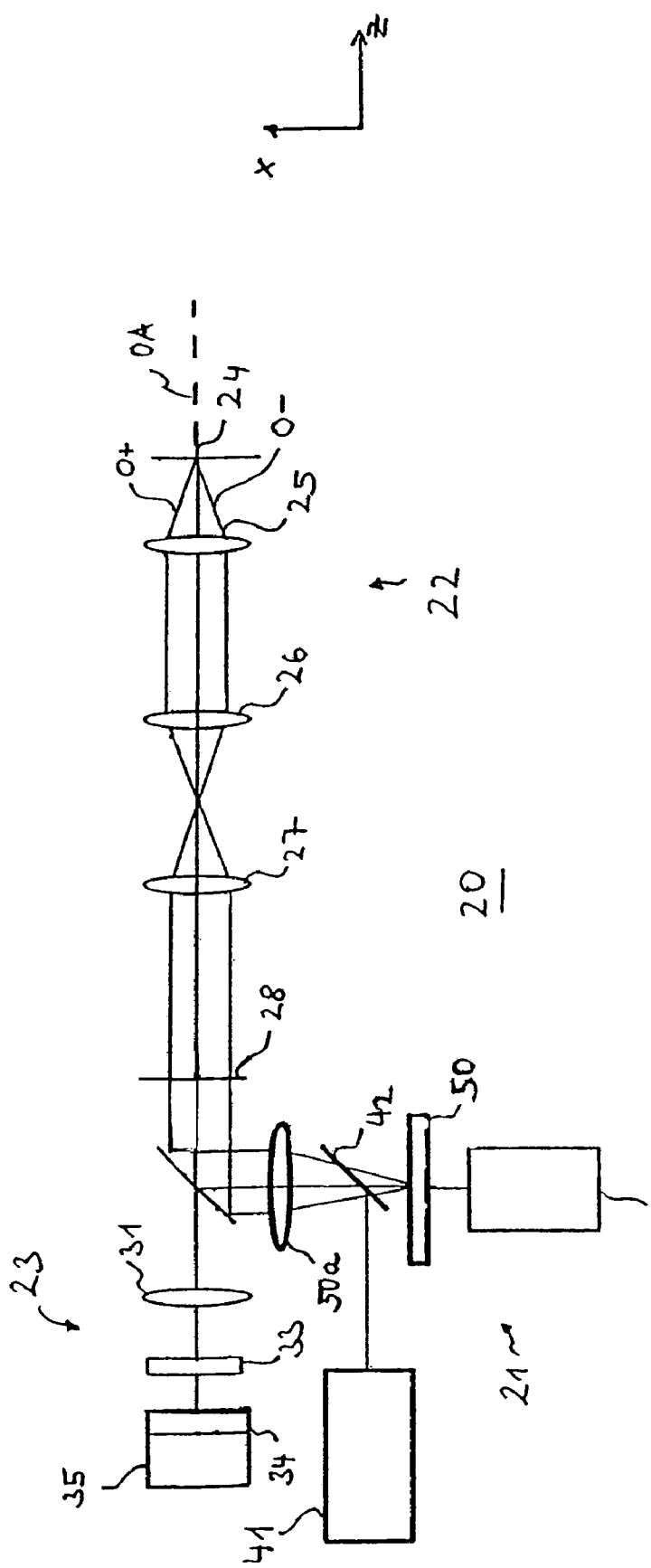
FIG. 13 shows a schematic representation of a third resolution-enhanced microscope.

FIG. 13 shows another modification of the laser scanning microscope 20 of FIG. 9a realizing one of the forms of methods with line-shaped illumination. In this case, too, elements identical with those of FIG. 9a have the same reference numerals assigned so that their description can be omitted again. Further, only the central rays are shown.

The now coherent light source 30 emits radiation through a grating 50 which generates two $1^{st}$ oders of diffraction, o+ and o−, as well as a $0^{th}$ order of diffraction. A cylindrical lens 50a, which is an example of an anamorphotic element here, is arranged following the grating. A line extending perpendicular to the optical axis is being focused on the sample.

During focusing, the orders of diffraction are incident such that they skim each other, thus resulting in interference in the sample. A so-called Talbot grating is generated along the optical axis OA due to the Talbot effect. This is shown schematically in the upper half of FIG. 14. The $+1^{th}$, the $0^{th}$ as well as the $-1^{th}$ order are incident in the sample 24 at different angles, and the interferences generate the Talbot structure known to the skilled person.

Figure 14:
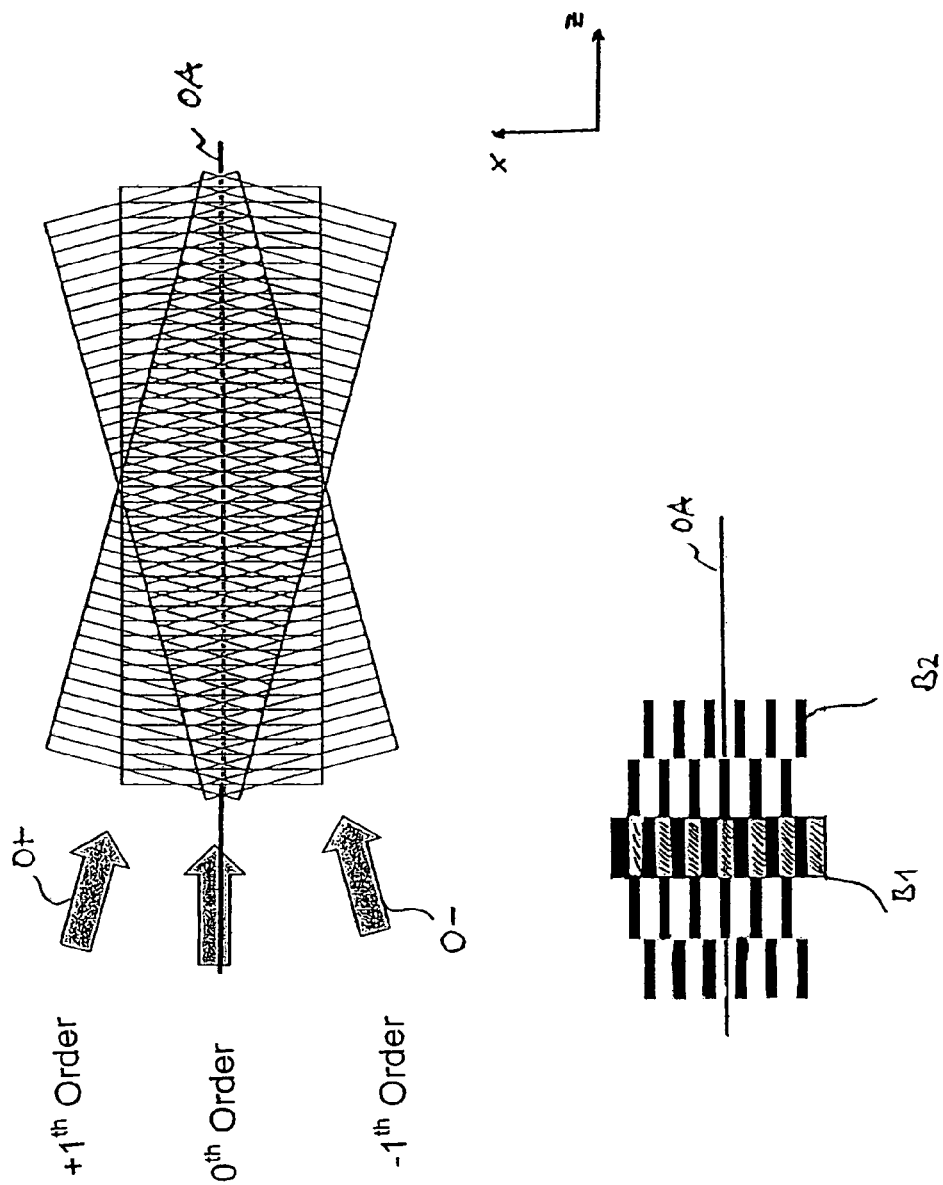
FIG. 14 shows a schematic representation of the third microscope's operation.

The effect within the sample is shown in the lower half of FIG. 14, which shows a thick cut (x,z plane) of the sample. At the locations of high intensity (black areas B2), the sample reaches the second state 6, i.e. depopulation of the excited states is achieved by switching the dye molecules. In the low-intensity areas B1, the sample remains in the first state 5 (hatched areas and white areas).

Detection is effected with a line detector 34 which is shown, by way of example, combined with the control device 35 in the construction of FIG. 13. Again, a block filter 33 (optional) is arranged preceding the line detector 34. Further, a slit-shaped stop (not shown in FIG. 13, because it is placed directly on the line detector 34) is arranged preceding the line detector 34 and located along the x-axis in order to cause the required confocal selection of a depth plane, thereby detecting only the hatched areas.

The scanner 28 enables movement of the exciting radiation distribution over the sample 24 perpendicular to the optical axis, i.e. along the x and y axes. Optionally, a homogeneous line can be generated, for example, along the x axis in the sample 24 by the resetting radiation source 41, said line enabling switching of the dyes from the second state 6 to the first state 5, as illustrated in FIG. 5. This line may also comprise an illumination pattern suitably located with respect to the sample areas B2 in the second state 6, because only these areas have to be reset.

Thus, the laser scanning microscope of FIG. 13 realizes the form of method of FIG. 8. The depth of the minima 45 can be set through the quality of the grating or by individual attenuation of individual orders.

Figure 15A:
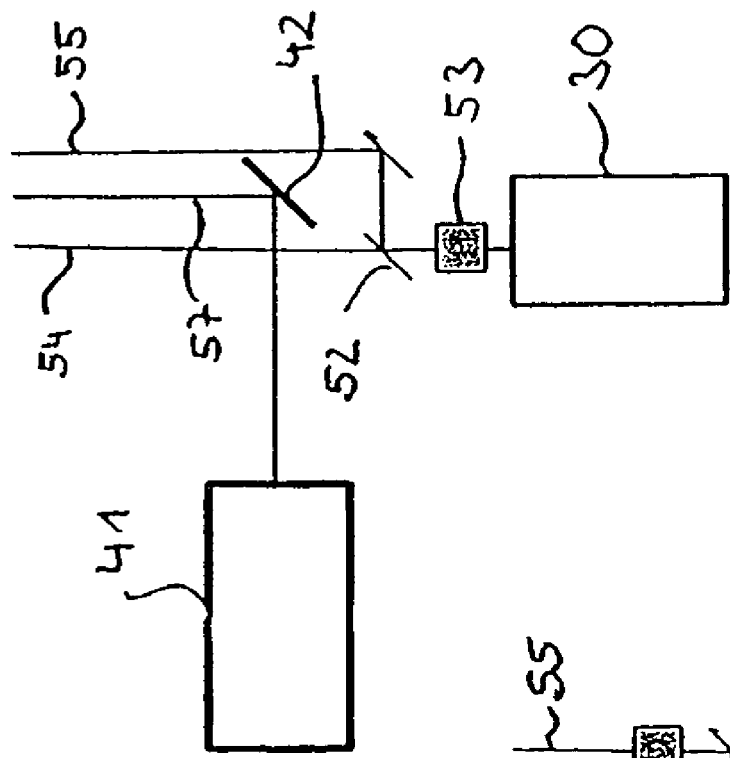
FIGS. 15a/b show schematic representations of parts of a fourth microscope.
Figure 15B:
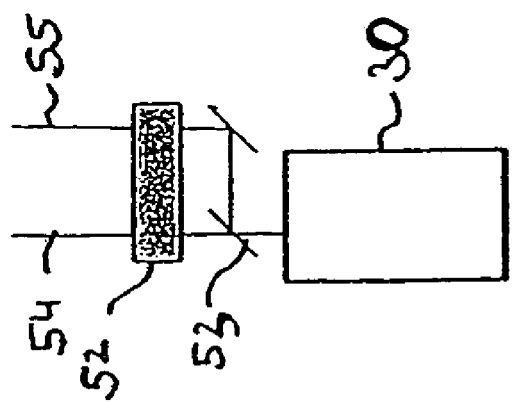

FIG. 15a shows an arrangement for realizing the form of method of FIG. 8b, which shows only the exciting module 21 of the laser scanning microscope 20 because, apart from that, the microscope module 22 has the structure already described. Two partial beams from the light source 30 are generated by means of a first beam splitter 53, which is perpendicularly spaced apart from the drawing plane here. A second beam splitter 52 generates a total of four partial beams extending in parallel. FIG. 15b shows the arrangement in a sectional view rotated by 90°. A total of four partial beams 54, 55 having the same intensity is present (the central beams are indicated here). In the drawing, two partial beams each take the same path, so that they are hidden.

Figure 16B:
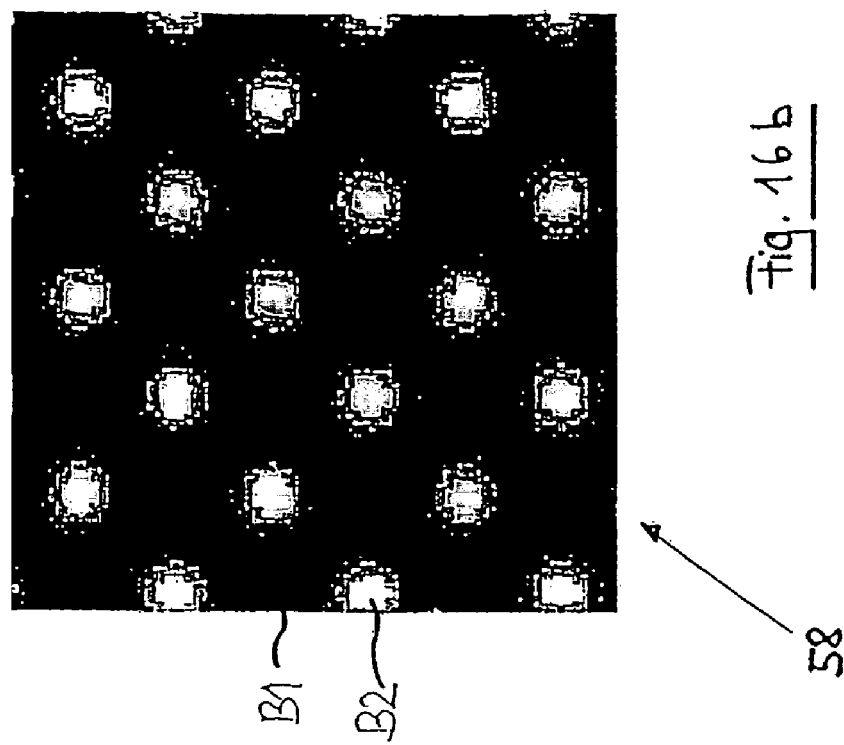
FIG. 16b shows multi-spot distribution realized with the fourth microscope.
Figure 16A:
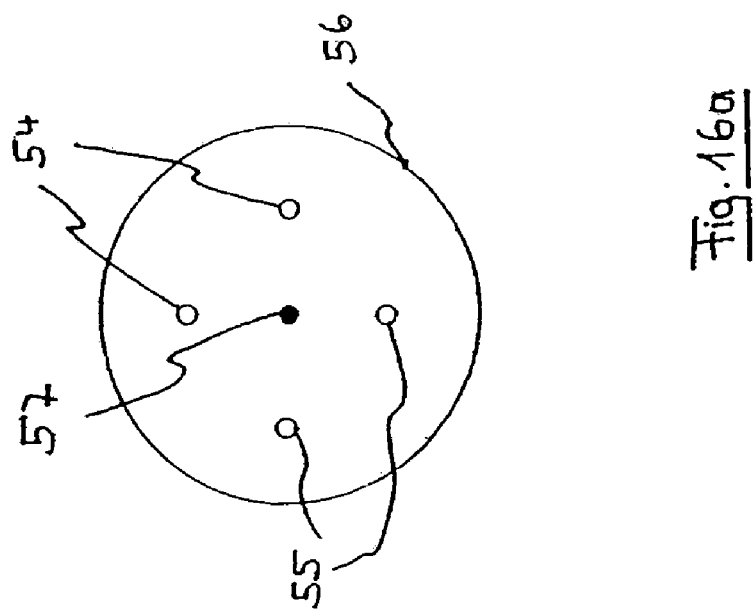
FIG. 16a shows a distribution of the exciting and resetting radiation, respectively, in a pupil of the fourth microscope.

The partial beams are focused into a pupil of the microscope module 22 by lenses such that the spot distribution shown in FIG. 16a is obtained within an edge 56 of the pupil. The four partial beams 55, 54 occupy the corners of a square. In the sample 24, the partial beams reach interference, whereby a multi-spot pattern 58 according to FIG. 16b is generated perpendicular to the optical axis on the sample 24. For example, the depth of the zeros of this multi-spot pattern 58 may be varied by modifying the intensities of the beams 54, 55 respectively located diagonally opposite each other. For this purpose, suitable adjustable attenuators (not shown) are provided for the partial beams.

Figure 17:
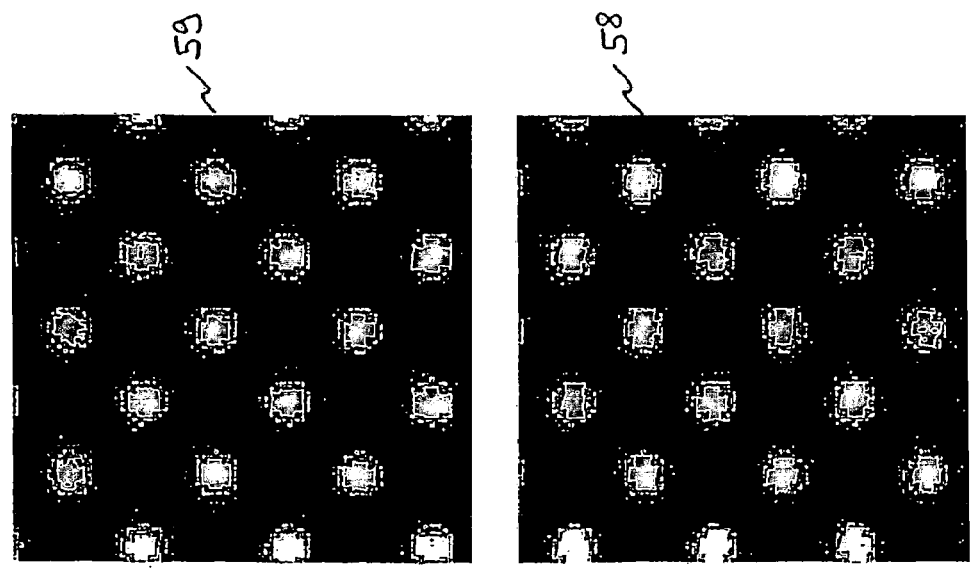
FIG. 17 shows fluorescence distribution in the fourth microscope.

At the locations of high intensity (bright areas B2) in the multi-spot pattern 58 of FIG. 16b, the sample 24 reaches the second state 6. Fluorescence radiation F is generated in the low-intensity areas B1 (dark areas). The fluorescence radiation F is then split as usual at the main color splitter 29. The detector 54 is a matrix detector adapted to the spot pattern and optionally comprising a preceding pinhole mask. The detector elements are aligned with the areas B1. The scanner 28 in turn enables shifting of the exciting radiation distribution over the sample 24 in the x and/or y direction. In the lower image, FIG. 17 shows the multi-spot pattern 58 and, moreover, the fluorescence pattern 59 excited thereby.

A further beam 57 can be focused in the pupil by the resetting light source 41, which beam thus illuminates a homogeneous area in the sample 24. Thus, resetting of the fluorescence molecules from the second state 6 to the first state 5 is effected, as already explained, between two scanning steps and, if required, also within one scanning step.

Figure 18:
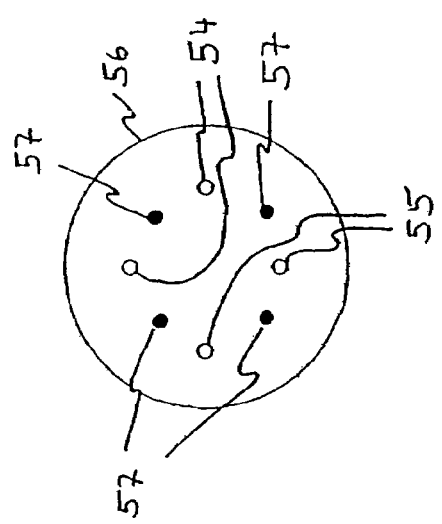
FIG. 18 shows distribution of the excitation and resetting radiation, respectively, in a pupil of a variant of the fourth microscope.

However, the resetting beam 47 may also comprise an illumination pattern which corresponds to the areas B2, because only these have to be reset. For this purpose, the beam 47 is also split up into four partial beams, in analogy with the partial beams 54, 55, and is imaged into the pupil so that, for example, the distribution shown in FIG. 18 results within the edge 56 of the pupil. In addition, the optical axis of the partial beams 57 of the resetting radiation R is tilted with respect to the optical axis of the exciting radiation A such that the minima of the multi-spot pattern 58 of the exciting radiation A which are generated in the sample coincide with the maxima of the multi-spot resetting pattern. The embodiment of FIG. 15a in the variant of FIG. 18 is a typical example of the fact that, by suitable structuring of the resetting radiation, sample- or dye-friendly resetting is effected only in the areas B2.

It is important that the sample is divided by suitable irradiation of exciting radiation A into areas B1 in the first state and areas B2 in the second state. Therefore, the conversion of sample areas into the second state can also be employed in order to select a depth plane of the sample (cf. FIG. 14), so that sample areas B1 cannot contribute to cross-talk of adjacent detector elements/detector regions.

For the method or microscope, respectively, described above in different variants, the setting of the power of the exciting radiation A as a function of the fluorescence characteristic of the sample is important, considering in particular the spatial distribution of the exciting radiation A. In particular, the depth of one or more minima 45 and the height of the corresponding maxima of the exciting radiation of the distribution determines the achievable resolution enhancement. Optimization of the setting of the spatial power distribution for the exciting radiation A can be realized in two ways: Knowing the characteristic curve 17, which has been/is being accordingly provided to the control device 35, for example, the optimum power level for a given spatial excitation distribution is calculated and set accordingly, for example by output of a desired value or even by direct control of the exciting module 21.

As an alternative or in addition, the actual resolution can be determined with a test preparation or a reference location on the sample to be examined, and the optimal power level can be determined in an interactive process for a given excitation distribution and then used for imaging the sample 24.

Instead of pure power scaling, the distribution can also be modified, of course, for example by accordingly setting the phase element 39.

The fluorescence characteristic of the sample 24, for example the fluorescence characteristic of a dye, can be determined by examining a test preparation or a reference location on the sample already under imaging conditions as they will be later. For this purpose, the power of the detected fluorescence radiation F is determined as a function of the power of the exciting radiation A at a point or a region of the sample. It is favorable for particularly good adjustment that the fluorescence characteristic, i.e. the characteristic curve 17, does not depend on the concentration of the fluorescent material, e.g. of the dye (as opposed to the emitted power of the fluorescence radiation F). For this purpose, the control device 35 of the scanning microscope 20 can automatically determine and accordingly adjust the optimal power from the determined curve 17 or from a supplied curve 17 or from a curve 17 stored in a memory.

Iterative determination is always advantageous where the fluorescence properties are strongly sample-dependent and a reference location for determining the fluorescence characteristic is present, or cannot be found, on the sample. In this case, it is possible to carry out, or to have the control device 35 carry out, power optimization either in a limited area within or outside of the sample field of interest or on the basis of imaging in the entire sample field to be imaged. The exciting power is optimized on the basis of a quality criterion of resolution (e.g. the contrast at a suitable location or the extent, in the Fourier space, of the frequency range transmitted in the image). It is generally sufficient to adapt the power in the minimum of the excitation distribution or a spatially widely distributed background power, respectively.

The exciting radiation A and the resetting radiation R can be generated from one single source of radiation. The source of radiation may either be directly switchable or may be provided with a subsequently arranged selecting arrangement.

The invention claimed is:

1. A resolution-enhanced luminescence microscopy method, wherein
a sample (P, 24) is excited to emit a given luminescence radiation (F) by irradiation of exciting radiation (A) and an image of the luminescent sample (P, 24) is obtained, wherein
the luminescent sample (P, 24) is transferable from a first state of luminescence (5), in which first state the sample's excitability for emission of the given luminescence radiation (F) increases up to a maximum value (18) as the exciting radiation power increases, into a second state of luminescence (6), in which second state the sample (P, 24) has reduced excitability for emission of the given luminescence radiation (F) relative to the first state (5), wherein the maximum value (18) is assigned to a threshold value (19) of exciting radiation power and the sample (P, 24) is transferable into the second state (6) by irradiation of exciting radiation power above the threshold value (19),
partial areas (B1) of the sample (P, 24) are brought into the first state (5) and adjacent partial areas (B2) thereof are brought into the second state (6), due to irradiation of exciting radiation (A) being effected with an exciting radiation distribution having at least one spatial power maximum above the threshold value (19) and at least one spatial, local power minimum (45) below the threshold value,
the image of the luminescent sample (P, 24) comprises sample areas (B1) being in the first state (5) and sample areas (B2) being in the second state (6), sample areas (B1) in the first state (5) contributing predominantly to the image of the luminescent sample (P, 24) and the image thus having an enhanced spatial resolution with respect to the exciting radiation distribution.

2. The method as claimed in claim 1, wherein the sample (P, 24) having been brought into the second state (6) returns to the first state (5) again, either by active influence or spontaneously.

3. The method as claimed in claim 2, wherein resetting radiation (R) is irradiated, which resets the sample (P, 24) from the second state (6) to the first state (5) and which has optical properties differing from the exciting radiation (A).

4. The method as claimed in claim 1, wherein the image is obtained by scanning the sample (P, 24) with a spot, line or multi-spot pattern (58), and in particular, resetting radiation (R) is provided between two scanning steps.

5. The method as claimed in claim 1, wherein a sample (P, 24) is used which does not luminesce at an exciting radiation power above the threshold value (19), emits luminescence radiation having other properties than the given luminescence radiation (F) and/or has modified properties leading to reduced luminescence.

6. The method as claimed in claim 1, wherein the exciting radiation distribution is diffraction-limited.

7. The method as claimed in claim 6, wherein toroidally distributed exciting radiation (A) is used and sample areas located outside the torus during detection of the luminescence radiation (F) are preferably blocked out in addition.

8. The method as claimed in claim 1, wherein the exciting radiation distribution (A) comprises line-shaped or planar structured sample illumination, in particular according to a strip grating or cross grating, as well as using spatially resolved detection to obtain an image.

9. The method as claimed in claim 1, wherein confocal detection (D) is carried out by sample areas (B1) being in the first state (5).

10. The method as claimed in claim 1, wherein depth resolution enhancement is effected along the optical axis (OA), due to the power minimum (45) below the threshold value (19) and the power maximum above the threshold (19) being adjacent to each other along the optical axis (OA).

11. The method as claimed in claim 1, wherein depth resolution enhancement is effected along the optical axis, due to exciting radiation (A) first being irradiated with a power above the threshold value into a depth region containing the focal plane, resetting radiation (R) being irradiated into the focal plane and exciting radiation (A) with the exciting radiation distribution then being irradiated, with the power minimum (45) located in the area of focus.

12. The method as claimed in claim 1, wherein either in sample areas (B1) having the first state (5), or in sample areas (B2) having the second state (6), the exciting radiation power is modulated according to a reference frequency and this reference frequency is used during detection of luminescence radiation by way of the lock-in technique.

13. The method as claimed in claim 12, wherein a low-resolution image is additionally obtained from a dc signal portion (S).

14. The method as claimed in claim 1, wherein a fluorescent sample (P, 24) is used, in a sample (P, 24) provided with at least one fluorophore.

15. The method as claimed in claim 1, wherein an image having exciting radiation distribution without a power minimum (45) below the threshold value is recorded and is used for subtraction.

16. The method as claimed in claim 1, wherein a characteristic curve of luminescence (17), which indicates emitted luminescence power as a function of the exciting radiation power, is evaluated, the threshold value (19) is determined therefrom and/or the exciting radiation distribution is selected depending on the characteristic curve.

17. The method as claimed in claim 1, wherein the exciting radiation distribution is iteratively optimized while evaluating the image resolution.

18. A microscope for resolution-enhanced luminescence microscopy, which comprises:
means (21, 22) for exciting luminescence which means irradiate exciting radiation (A) onto the sample (P, 24) and thus excite the emission of given luminescence radiation (F) in the sample (P, 24),
means (22, 23) for obtaining an image of the luminescent sample (P, 24),
wherein the exciting means irradiate the exciting radiation (A) with a given exciting radiation distribution having at least one spatial power maximum which is located above a threshold value (19) and at least one spatial, local power minimum (45) which is located below the threshold value (19),
wherein the threshold value (19) separates two luminescence regions (5, 6) of the sample (P, 24), a first state region (5) which is present at exciting radiation powers below the threshold value (19) and in which excitability for emission of the given luminescence radiation (F) increases up to a maximum value (18), which is reached at the threshold value (19), as the exciting radiation power increases, and a second state region (6), which is present during and/or after exciting radiation powers above the threshold value (19) and in which the sample (P, 24) has reduced excitability for emission of the given luminescence radiation (F) relative to the first region (5), and
wherein the means for imaging detect sample areas (B1) in the first region (5), which have been irradiated with exciting radiation power below the threshold value (19), and sample areas (B2) in the second region (6), which have been irradiated with exciting radiation power above the threshold value (19), wherein predominantly sample areas (B1) in the first region (5) contribute to the image of the sample and the image thereby has enhanced spatial resolution relative to the exciting radiation distribution.

19. The microscope as claimed in claim 18, comprising an exciting radiation source (30), which emits the exciting radiation (A), and a unit (36-40) arranged following the exciting radiation source and emitting an exciting beam which has a beam profile with the power minimum (45) having an exciting radiation power located below the threshold value (19).

20. The microscope as claimed in claim 18, wherein a scanning unit (28) raster-scans the sample (P, 24) with exciting radiation (A).

21. The microscope as claimed in claim 20, wherein the exciting radiation distribution comprises at least one diffraction-limited spot image.

22. The microscope as claimed in claim 21, wherein the exciting radiation distribution illuminates at least one line-shaped or strip- or grid-shaped sample area with exciting radiation (A), the exciting radiation power being located above the threshold value in some parts of the strip or of the grid and below the threshold value (19) in other parts of the strip or grid, respectively.

23. The microscope as claimed in claim 18, wherein the exciting radiation distribution, the spatial power minimum (45) and the spatial power minimum are adjacent each other along the optical axis (OA).

24. The microscope as claimed in claim 18, characterized by means (41, 42) for resetting the sample (24) from the second state region (6) to the first state region (5), said means comprising a radiation source (41) emitting resetting radiation (R) with optical properties differing from the exciting radiation (A), and optics (42) for coupling-in of the resetting radiation (R).

25. The microscope as claimed in claim 18, characterized by an intensity modulator (37,38,49,35), which modulates the distribution of the exciting radiation (A) using a reference frequency and a lock-in amplifier (48) which is provided in the means for imaging or is connected thereto and which evaluates the reference frequency and reduces background radiation (S).

26. The microscope as claimed in claim 25, comprising a common signal output for obtaining an additional low-resolution image.

27. The microscope as claimed in claim 18 comprising a control device (35) which controls the microscope for execution of one of the methods as claimed in any one of claims 1 to 17.

28. The microscope as claimed in claim 18, comprising a control device (35) which controls or reads out, respectively, the means for excitation and the means for imaging and adjusts the exciting radiation distribution so as to optimize image resolution.

29. The microscope as claimed in claim 28, wherein the control device (35) comprises a storage or data input unit through which a characteristic curve of luminescence (17) is available to the control device, said characteristic curve of luminescence (17) indicating the emitted luminescence power as a function of the exciting radiation power and said control device (35) determining the threshold value (19) from the characteristic curve of luminescence (17) and/or setting the exciting radiation distribution as a function of the characteristic curve.

30. The microscope as claimed in claim 28, wherein the control device (35) determines the resolution from the image of the sample (P, 24) and iteratively sets the exciting radiation distribution so as to optimize image resolution.

* * * * *